US008459509B2

(12) United States Patent
Bui

(10) Patent No.: US 8,459,509 B2
(45) Date of Patent: Jun. 11, 2013

(54) FLUID DISPENSING APPARATUS

(75) Inventor: Xuan S. Bui, Culver City, CA (US)

(73) Assignee: Sakura Finetek U.S.A., Inc., Torrance, CA (US)

( * ) Notice: Subject to any disclaimer, the term of this patent is extended or adjusted under 35 U.S.C. 154(b) by 530 days.

(21) Appl. No.: 11/441,668

(22) Filed: May 25, 2006

(65) Prior Publication Data

US 2007/0272710 A1    Nov. 29, 2007

(51) Int. Cl.
*B65D 37/00* (2006.01)
(52) U.S. Cl.
USPC ........... 222/207; 222/383.1; 222/181.1; 222/325; 436/180
(58) Field of Classification Search
USPC .......... 222/207, 100, 213, 442, 450, 633, 222/496, 189.1, 189.11, 189.06, 383.1, 209; 222/214, 494, 181.1, 476, 325; 210/452; 422/100, 63; 251/12; 137/510; 436/180
See application file for complete search history.

(56) References Cited

U.S. PATENT DOCUMENTS

| | | | | |
|---|---|---|---|---|
| 1,621,097 | A | * | 3/1927 | Zammataro .................. 222/496 |
| 2,709,025 | A | | 5/1955 | Scott |
| 2,772,817 | A | * | 12/1956 | Jauch ............................ 222/207 |
| 3,008,611 | A | * | 11/1961 | Mancusi, Jr. .................. 222/207 |
| 3,294,290 | A | | 12/1966 | Erickson et al. |
| 3,881,641 | A | | 5/1975 | Pliml, Jr. et al. |
| 3,904,079 | A | | 9/1975 | Kross |
| 3,987,938 | A | * | 10/1976 | Cooprider et al. ............ 222/209 |
| 4,018,363 | A | | 4/1977 | Cassia |
| 4,025,241 | A | | 5/1977 | Clemens |
| 4,039,775 | A | | 8/1977 | Andra |
| 4,099,483 | A | | 7/1978 | Henderson |
| 4,149,573 | A | | 4/1979 | Cassia |
| 4,149,633 | A | | 4/1979 | Nilson |
| 4,199,558 | A | | 4/1980 | Henderson |
| 4,258,759 | A | | 3/1981 | Achen |
| 4,345,627 | A | | 8/1982 | Cassia |
| 4,356,727 | A | | 11/1982 | Brown et al. |

(Continued)

FOREIGN PATENT DOCUMENTS

| | | |
|---|---|---|
| AU | 2004266226 | 3/2005 |
| CN | 2390207 Y | 8/2000 |

(Continued)

OTHER PUBLICATIONS

Translation of DE 385159.*

(Continued)

*Primary Examiner* — Kevin P Shaver
*Assistant Examiner* — Robert Nichols, II
(74) *Attorney, Agent, or Firm* — Blakely Sokoloff Taylor & Zafman LLP

(57) ABSTRACT

A fluid dispensing apparatus includes a fluid reservoir and a dispensing assembly. The dispensing assembly includes a housing and a deformable member that define a metering chamber that is configured to receive a predetermined volume of fluid from the fluid reservoir. The deformable member is deformed from a rest position to an eject position and the deformation causes the volume of the metering chamber to change which results in a change in fluid pressure within the metering chamber. An increase in the fluid pressure within metering chamber causes a predetermined volume of fluid within the metering chamber to be ejected and a decrease in the fluid pressure within the metering chamber causes fluid to be drawn into the metering chamber from the reservoir.

14 Claims, 13 Drawing Sheets

U.S. PATENT DOCUMENTS

| | | | |
|---|---|---|---|
| 4,440,323 A * | 4/1984 | Benson | 222/209 |
| 4,561,571 A * | 12/1985 | Chen | 222/207 |
| 4,604,964 A | 8/1986 | Gordon et al. | |
| 4,615,476 A * | 10/1986 | Hobbs et al. | 222/153.09 |
| 4,667,854 A | 5/1987 | McDermott et al. | |
| 4,673,109 A | 6/1987 | Cassia | |
| 4,678,752 A | 7/1987 | Thorne et al. | |
| 4,722,372 A | 2/1988 | Hoffman et al. | |
| 4,731,335 A | 3/1988 | Brigati | |
| 4,741,898 A | 5/1988 | Mallik et al. | |
| 4,764,342 A | 8/1988 | Kelln et al. | |
| 4,790,640 A | 12/1988 | Nason | |
| 4,798,311 A | 1/1989 | Workum | |
| 4,801,431 A | 1/1989 | Cuomo et al. | |
| 4,834,019 A | 5/1989 | Gordon et al. | |
| 4,838,457 A | 6/1989 | Swahl et al. | |
| 4,846,636 A | 7/1989 | Danby et al. | |
| 4,867,347 A | 9/1989 | Wass et al. | |
| 4,880,149 A | 11/1989 | Scholefield et al. | |
| 4,886,192 A | 12/1989 | Cassia | |
| 4,917,265 A * | 4/1990 | Chiang | 222/52 |
| 4,921,136 A | 5/1990 | Roggenburg, Jr. | |
| 4,927,061 A | 5/1990 | Leigh et al. | |
| 4,946,076 A | 8/1990 | Hackmann et al. | |
| 4,955,512 A | 9/1990 | Sharples | |
| 4,961,508 A | 10/1990 | Weimer et al. | |
| 4,969,581 A | 11/1990 | Seifert et al. | |
| 4,972,978 A | 11/1990 | DeLuca | |
| 4,974,754 A | 12/1990 | Wirz | |
| 4,978,036 A | 12/1990 | Burd | |
| 4,985,206 A | 1/1991 | Bowman et al. | |
| 5,002,736 A | 3/1991 | Babbitt et al. | |
| 5,033,656 A | 7/1991 | Blette et al. | |
| 5,035,350 A | 7/1991 | Blette et al. | |
| 5,068,091 A | 11/1991 | Toya | |
| 5,073,504 A | 12/1991 | Bogen | |
| 5,082,150 A * | 1/1992 | Steiner et al. | 222/189.09 |
| 5,225,325 A | 7/1993 | Miller et al. | |
| 5,232,664 A | 8/1993 | Krawzak et al. | |
| 5,242,081 A | 9/1993 | van der Heyden et al. | |
| 5,242,083 A | 9/1993 | Christine et al. | |
| 5,244,787 A | 9/1993 | Key et al. | |
| 5,252,293 A | 10/1993 | Drbal et al. | |
| 5,253,774 A | 10/1993 | Honig et al. | |
| 5,255,822 A | 10/1993 | Mease et al. | |
| 5,273,905 A | 12/1993 | Muller et al. | |
| 5,275,309 A | 1/1994 | Baron et al. | |
| 5,316,452 A | 5/1994 | Bogen et al. | |
| 5,322,771 A | 6/1994 | Rybski et al. | |
| 5,338,358 A | 8/1994 | Mizusawa et al. | |
| 5,355,439 A | 10/1994 | Bernstein et al. | |
| 5,356,039 A | 10/1994 | Christine et al. | |
| 5,390,822 A | 2/1995 | Lataix | |
| 5,418,138 A | 5/1995 | Miller et al. | |
| 5,421,489 A * | 6/1995 | Holzner et al. | 222/207 |
| 5,424,036 A | 6/1995 | Ushikubo | |
| 5,425,918 A | 6/1995 | Healey et al. | |
| 5,433,351 A | 7/1995 | Okuyama et al. | |
| 5,439,649 A | 8/1995 | Tseung et al. | |
| 5,474,212 A * | 12/1995 | Ichikawa et al. | 222/105 |
| 5,525,300 A | 6/1996 | Danssaert et al. | |
| 5,534,114 A | 7/1996 | Cutright et al. | |
| 5,561,556 A | 10/1996 | Weissman et al. | |
| 5,578,452 A | 11/1996 | Shi et al. | |
| 5,579,945 A * | 12/1996 | Ichikawa et al. | 220/495.06 |
| 5,580,523 A | 12/1996 | Bard | |
| 5,595,707 A | 1/1997 | Copeland et al. | |
| 5,602,674 A | 2/1997 | Weissman et al. | |
| 5,609,822 A | 3/1997 | Carey et al. | |
| 5,626,262 A | 5/1997 | Fitten et al. | |
| 5,639,423 A | 6/1997 | Northrup et al. | |
| 5,645,114 A | 7/1997 | Bogen et al. | |
| 5,650,327 A | 7/1997 | Copeland et al. | |
| 5,654,199 A | 8/1997 | Copeland et al. | |
| 5,654,200 A | 8/1997 | Copeland et al. | |
| 5,675,715 A | 10/1997 | Bernstein et al. | |
| 5,700,346 A | 12/1997 | Edwards | |
| 5,810,204 A | 9/1998 | Devlin et al. | |
| 5,819,842 A | 10/1998 | Potter et al. | |
| 5,836,482 A | 11/1998 | Ophardt et al. | |
| 5,839,091 A | 11/1998 | Rhett et al. | |
| 5,843,700 A | 12/1998 | Kerrod et al. | |
| 5,846,396 A | 12/1998 | Zanzucchi et al. | |
| 5,851,488 A | 12/1998 | Saul et al. | |
| 5,855,302 A | 1/1999 | Fisscher | |
| 5,857,595 A | 1/1999 | Nilson | |
| 5,885,530 A | 3/1999 | Babson et al. | |
| 5,947,167 A | 9/1999 | Bogen et al. | |
| 5,948,359 A | 9/1999 | Kalra et al. | |
| 5,950,874 A | 9/1999 | Sindoni | |
| 5,950,878 A | 9/1999 | Wade et al. | |
| 5,954,167 A | 9/1999 | Richardson et al. | |
| 5,958,341 A | 9/1999 | Chu | |
| 5,964,454 A | 10/1999 | Volpel | |
| 5,965,454 A | 10/1999 | Farmilo et al. | |
| 5,968,731 A | 10/1999 | Layne et al. | |
| 5,971,223 A | 10/1999 | Fisscher | |
| 6,001,309 A | 12/1999 | Gamble et al. | |
| 6,012,613 A * | 1/2000 | Chen | 222/207 |
| 6,017,495 A | 1/2000 | Ljungmann | |
| 6,020,995 A | 2/2000 | Dreyer et al. | |
| 6,045,759 A | 4/2000 | Ford et al. | |
| 6,076,583 A | 6/2000 | Edwards | |
| 6,092,695 A | 7/2000 | Loeffler | |
| 6,093,574 A | 7/2000 | Druyor-Sanchez et al. | |
| 6,096,271 A | 8/2000 | Bogen et al. | |
| 6,180,061 B1 | 1/2001 | Bogen et al. | |
| 6,183,693 B1 | 2/2001 | Bogen et al. | |
| 6,189,740 B1 | 2/2001 | Wade et al. | |
| 6,192,945 B1 | 2/2001 | Ford et al. | |
| 6,206,238 B1 | 3/2001 | Ophardt | |
| 6,216,916 B1 | 4/2001 | Maddox et al. | |
| 6,238,910 B1 | 5/2001 | Custance et al. | |
| 6,244,474 B1 | 6/2001 | Loeffler | |
| 6,259,956 B1 | 7/2001 | Myers et al. | |
| 6,273,298 B1 | 8/2001 | Post | |
| 6,286,725 B1 * | 9/2001 | Gerber | 222/207 |
| 6,296,809 B1 | 10/2001 | Richards et al. | |
| 6,335,166 B1 | 1/2002 | Ammann et al. | |
| 6,343,716 B1 | 2/2002 | Baudin et al. | |
| 6,349,264 B1 | 2/2002 | Rhett et al. | |
| 6,352,861 B1 | 3/2002 | Copeland et al. | |
| 6,387,326 B1 | 5/2002 | Edwards et al. | |
| 6,415,961 B2 | 7/2002 | Bonningue | |
| 6,416,713 B1 | 7/2002 | Ford et al. | |
| 6,451,551 B1 | 9/2002 | Zhan et al. | |
| 6,472,217 B1 | 10/2002 | Richards et al. | |
| 6,489,171 B1 | 12/2002 | Aghassi et al. | |
| 6,495,106 B1 | 12/2002 | Kalra et al. | |
| 6,516,620 B2 | 2/2003 | Lang | |
| 6,534,008 B1 | 3/2003 | Angros | |
| 6,540,117 B2 | 4/2003 | Powling | |
| 6,541,261 B1 | 4/2003 | Bogen et al. | |
| 6,543,652 B1 | 4/2003 | Kelder et al. | |
| 6,544,798 B1 | 4/2003 | Christensen et al. | |
| 6,553,145 B1 | 4/2003 | Kang et al. | |
| 6,580,056 B1 | 6/2003 | Tacha | |
| 6,582,962 B1 | 6/2003 | Richards et al. | |
| 6,594,537 B1 | 7/2003 | Bernstein et al. | |
| 6,605,213 B1 | 8/2003 | Ammann et al. | |
| 6,607,103 B2 | 8/2003 | Gerenraich et al. | |
| 6,632,598 B1 | 10/2003 | Zhang et al. | |
| 6,635,225 B1 | 10/2003 | Thiem et al. | |
| 6,673,620 B1 | 1/2004 | Loeffler et al. | |
| 6,703,247 B1 | 3/2004 | Chu | |
| 6,720,888 B2 | 4/2004 | Eagleson et al. | |
| 6,729,502 B2 | 5/2004 | Lewis et al. | |
| 6,735,531 B2 | 5/2004 | Rhett et al. | |
| 6,746,851 B1 | 6/2004 | Tseung et al. | |
| 6,758,360 B2 | 7/2004 | Van Giezen et al. | |
| 6,783,733 B2 | 8/2004 | Bogen et al. | |
| 6,805,264 B2 * | 10/2004 | Houvras | 222/180 |
| 6,827,900 B2 | 12/2004 | Thiem et al. | |
| 6,827,901 B2 | 12/2004 | Copeland et al. | |
| 6,855,292 B2 | 2/2005 | Angros | |
| 6,855,552 B2 | 2/2005 | Towne et al. | |
| 6,855,559 B1 | 2/2005 | Christensen et al. | |

| Patent No. | Date | Name |
|---|---|---|
| 6,899,283 B2 | 5/2005 | Ohnishi et al. |
| 6,943,029 B2 | 9/2005 | Copeland et al. |
| 6,945,128 B2 | 9/2005 | Ford et al. |
| 6,991,934 B2 | 1/2006 | Walton et al. |
| 6,998,270 B2 | 2/2006 | Tseung et al. |
| 7,007,824 B2 | 3/2006 | Danby et al. |
| 7,025,937 B2 | 4/2006 | Plank |
| 7,057,808 B2 | 6/2006 | Dooling |
| 7,070,951 B2 | 7/2006 | Zhang et al. |
| 7,083,106 B2 | 8/2006 | Albany |
| 7,118,918 B2 | 10/2006 | Copeland et al. |
| 7,156,814 B1 | 1/2007 | Williamson et al. |
| 7,165,722 B2 | 1/2007 | Shafer et al. |
| 7,169,601 B1 | 1/2007 | Northrup et al. |
| 7,178,416 B2 | 2/2007 | Whelan et al. |
| 7,179,424 B2 | 2/2007 | Williamson, IV et al. |
| 7,187,286 B2 | 3/2007 | Morris et al. |
| 7,199,712 B2 | 4/2007 | Tafas et al. |
| 7,201,295 B1 | 4/2007 | Sitzberger |
| 7,209,042 B2 | 4/2007 | Martin et al. |
| 7,217,392 B2 | 5/2007 | Bogen et al. |
| 7,220,589 B2 | 5/2007 | Richards et al. |
| 7,226,788 B2 | 6/2007 | De La Torre-Bueno |
| 7,233,250 B2 | 6/2007 | Forster |
| 7,250,301 B2 | 7/2007 | Angros |
| 7,264,142 B2 * | 9/2007 | Py .............................. 222/321.7 |
| 7,270,785 B1 | 9/2007 | Lemme et al. |
| 7,275,682 B2 | 10/2007 | Excoffier et al. |
| 7,278,554 B2 | 10/2007 | Armstrong |
| 7,294,478 B1 | 11/2007 | Hinchcliffe |
| 7,303,725 B2 | 12/2007 | Reinhardt et al. |
| 7,314,238 B2 | 1/2008 | Robert |
| 7,323,491 B2 * | 1/2008 | Lohray et al. ................. 514/427 |
| 7,338,803 B2 | 3/2008 | Mizzer et al. |
| 7,382,258 B2 | 6/2008 | Oldham et al. |
| 7,395,974 B2 | 7/2008 | Albany |
| 7,400,983 B2 | 7/2008 | Feingold et al. |
| 7,405,056 B2 | 7/2008 | Lam et al. |
| 7,425,306 B1 | 9/2008 | Kram |
| 7,435,381 B2 | 10/2008 | Pugia et al. |
| 7,435,383 B2 | 10/2008 | Tseung et al. |
| 7,468,161 B2 | 12/2008 | Reinhardt et al. |
| 7,470,401 B2 | 12/2008 | Morales |
| 7,470,541 B2 | 12/2008 | Copeland et al. |
| 7,476,362 B2 | 1/2009 | Angros |
| 7,501,283 B2 | 3/2009 | Hersch et al. |
| 7,553,672 B2 | 6/2009 | Bogen |
| 7,584,019 B2 | 9/2009 | Feingold et al. |
| 7,593,787 B2 | 9/2009 | Feingold et al. |
| 7,603,201 B2 | 10/2009 | Feingold et al. |
| 7,622,077 B2 | 11/2009 | Angros |
| 7,632,461 B2 | 12/2009 | Angros |
| 7,639,139 B2 | 12/2009 | Tafas et al. |
| 7,642,093 B2 | 1/2010 | Tseung et al. |
| 7,651,010 B2 | 1/2010 | Orzech et al. |
| 7,718,435 B1 | 5/2010 | Bogen et al. |
| 7,722,811 B2 | 5/2010 | Konrad et al. |
| 7,744,817 B2 | 6/2010 | Bui |
| 7,760,428 B2 | 7/2010 | Sieckmann |
| 7,838,283 B2 | 11/2010 | Erickson et al. |
| 7,850,912 B2 | 12/2010 | Favuzzi et al. |
| 7,880,617 B2 | 2/2011 | Morris et al. |
| 7,887,755 B2 | 2/2011 | Mingerink et al. |
| 7,897,106 B2 | 3/2011 | Angros |
| 7,901,941 B2 | 3/2011 | Tseung et al. |
| 7,922,986 B2 | 4/2011 | Byrnard et al. |
| 7,937,228 B2 | 5/2011 | Feingold et al. |
| 7,951,612 B2 | 5/2011 | Angros |
| 7,960,178 B2 | 6/2011 | Key et al. |
| 8,007,720 B2 | 8/2011 | Angros |
| 8,007,721 B2 | 8/2011 | Angros |
| 8,039,262 B2 | 10/2011 | Konrad et al. |
| 8,052,927 B2 | 11/2011 | Angros |
| 8,058,010 B2 | 11/2011 | Erickson et al. |
| 8,071,023 B2 | 12/2011 | Angros |
| 8,071,026 B2 | 12/2011 | Rapp et al. |
| 8,092,742 B2 | 1/2012 | Angros |
| 8,137,619 B2 | 3/2012 | Ford et al. |
| 8,142,739 B2 | 3/2012 | Tseung et al. |
| 2001/0044603 A1 | 11/2001 | Harold |
| 2002/0013194 A1 | 1/2002 | Kitano et al. |
| 2002/0079318 A1 | 6/2002 | Wurzinger |
| 2002/0110494 A1 | 8/2002 | Lemme et al. |
| 2002/0114733 A1 | 8/2002 | Copeland et al. |
| 2002/0182115 A1 | 12/2002 | Aghassi et al. |
| 2003/0100043 A1 | 5/2003 | Kalra et al. |
| 2003/0157545 A1 | 8/2003 | Jevons et al. |
| 2003/0203493 A1 | 10/2003 | Lemme et al. |
| 2004/0033163 A1 | 2/2004 | Tseung et al. |
| 2004/0033169 A1 | 2/2004 | Shah |
| 2004/0091395 A1 | 5/2004 | Ward et al. |
| 2004/0120862 A1 | 6/2004 | Lang et al. |
| 2004/0191128 A1 | 9/2004 | Bogen et al. |
| 2004/0197230 A1 | 10/2004 | Lemme et al. |
| 2004/0266015 A1 | 12/2004 | Favuzzi et al. |
| 2005/0019902 A1 | 1/2005 | Mathies et al. |
| 2005/0035156 A1 * | 2/2005 | Hersch et al. ................. 222/504 |
| 2005/0064535 A1 | 3/2005 | Favuzzi et al. |
| 2005/0135972 A1 | 6/2005 | Lemme et al. |
| 2005/0150911 A1 | 7/2005 | Bach |
| 2005/0153453 A1 | 7/2005 | Copeland et al. |
| 2005/0164374 A1 | 7/2005 | Kram |
| 2005/0186114 A1 | 8/2005 | Reinhardt et al. |
| 2005/0191214 A1 | 9/2005 | Tseung et al. |
| 2005/0250211 A1 | 11/2005 | Reinhardt et al. |
| 2005/0281711 A1 | 12/2005 | Testa et al. |
| 2006/0019332 A1 | 1/2006 | Zhang et al. |
| 2006/0040341 A1 | 2/2006 | Bland et al. |
| 2006/0045806 A1 | 3/2006 | Winther et al. |
| 2006/0063265 A1 | 3/2006 | Welcher et al. |
| 2006/0088928 A1 | 4/2006 | Sweet et al. |
| 2006/0088940 A1 | 4/2006 | Feingold et al. |
| 2006/0105359 A1 | 5/2006 | Favuzzi et al. |
| 2006/0120921 A1 | 6/2006 | Elliot et al. |
| 2006/0127283 A1 | 6/2006 | Tseung et al. |
| 2006/0134793 A1 | 6/2006 | Key et al. |
| 2006/0147351 A1 | 7/2006 | Falb et al. |
| 2006/0148063 A1 | 7/2006 | Fauzzi et al. |
| 2006/0151051 A1 | 7/2006 | Py et al. |
| 2006/0169719 A1 | 8/2006 | Bui |
| 2006/0172426 A1 | 8/2006 | Buchanan |
| 2006/0190185 A1 | 8/2006 | Ford et al. |
| 2006/0191952 A1 | 8/2006 | Kalra et al. |
| 2006/0252025 A1 | 11/2006 | Nitta et al. |
| 2006/0263268 A9 | 11/2006 | Tseung et al. |
| 2006/0265133 A1 | 11/2006 | Cocks et al. |
| 2006/0269985 A1 | 11/2006 | Kitayama |
| 2007/0010912 A1 | 1/2007 | Feingold et al. |
| 2007/0038491 A1 | 2/2007 | Samuhel et al. |
| 2007/0068969 A1 | 3/2007 | Orzech et al. |
| 2007/0160494 A1 | 7/2007 | Sands |
| 2007/0270714 A1 | 11/2007 | Cushner et al. |
| 2007/0272710 A1 | 11/2007 | Bui |
| 2008/0102006 A1 | 5/2008 | Kram et al. |
| 2008/0118378 A1 | 5/2008 | Baron et al. |
| 2008/0135583 A1 * | 6/2008 | Caswell et al. ............... 222/333 |
| 2008/0215625 A1 | 9/2008 | Veitch et al. |
| 2008/0217246 A1 | 9/2008 | Benn et al. |
| 2008/0226508 A1 | 9/2008 | Byrnard et al. |
| 2008/0235055 A1 | 9/2008 | Mattingly et al. |
| 2008/0254023 A1 | 10/2008 | Ljungmann et al. |
| 2008/0286753 A1 * | 11/2008 | Erickson et al. .................. 435/5 |
| 2008/0305515 A1 | 12/2008 | Burgart et al. |
| 2009/0004691 A1 | 1/2009 | Erickson et al. |
| 2009/0028757 A1 | 1/2009 | Lihl et al. |
| 2009/0241751 A1 | 10/2009 | Walter |
| 2009/0308887 A1 | 12/2009 | Woo et al. |
| 2009/0325309 A1 | 12/2009 | Favuzzi et al. |
| 2010/0017030 A1 | 1/2010 | Feingold et al. |
| 2010/0028978 A1 | 2/2010 | Angros |
| 2010/0068757 A1 | 3/2010 | Angros |
| 2010/0099133 A1 | 4/2010 | Egle et al. |
| 2010/0178668 A1 | 7/2010 | Elliot et al. |
| 2011/0079615 A1 | 4/2011 | Ophardt et al. |
| 2011/0167930 A1 | 7/2011 | Feingold et al. |
| 2011/0176977 A1 | 7/2011 | Tseung et al. |
| 2011/0269238 A1 | 11/2011 | Key et al. |
| 2012/0003679 A1 | 1/2012 | Haberkorn |

FOREIGN PATENT DOCUMENTS

| | | | |
|---|---|---|---|
| DE | 385159 | * | 11/1923 |
| DE | 3902476 A | * | 8/1990 |
| EP | 0185330 | | 6/1986 |
| EP | 0557871 | | 9/1993 |
| EP | 1028320 | | 8/2000 |
| GB | 2037255 | | 7/1980 |
| JP | 61200966 | | 12/1986 |
| JP | 3148067 | | 6/1991 |
| JP | 6-510860 | | 12/1994 |
| JP | 9-503060 | | 3/1997 |
| JP | 10-501167 | | 2/1998 |
| JP | 11170558 | | 6/1999 |
| JP | 11258243 | | 9/1999 |
| JP | 2000167318 | * | 6/2000 |
| JP | 2001-509727 | | 7/2001 |
| JP | 2001-512823 | | 8/2001 |
| JP | 2001-522033 | | 11/2001 |
| JP | 2002507738 | | 3/2002 |
| JP | 2002-522065 | | 7/2002 |
| JP | 2003-057246 | | 2/2003 |
| JP | 2004-533605 | | 11/2004 |
| WO | WO 95/08774 | | 3/1995 |
| WO | WO 95/26796 | | 10/1995 |
| WO | WO 96/39260 | | 12/1996 |
| WO | WO 99/08090 | | 2/1999 |
| WO | WO 99/22867 | | 5/1999 |
| WO | WO 00/09650 | | 2/2000 |
| WO | WO 00/12994 | | 3/2000 |
| WO | WO 01/41918 | | 6/2001 |
| WO | WO 02/072264 | | 9/2002 |
| WO | WO 03/054553 | | 7/2003 |
| WO | WO 03/091710 | | 11/2003 |
| WO | WO 03/106033 | | 12/2003 |
| WO | WO 2004/059288 | | 7/2004 |
| WO | WO 2004/074847 | | 9/2004 |
| WO | WO 2005/000731 | | 1/2005 |

OTHER PUBLICATIONS

English translation of DE 385 159.*
European Search Report for EP Appln No. 06101495.7, mailed Dec. 18, 2006 (10 pages).
European Search Report for EP Appln No. 06101497.3, mailed Jun. 20, 2006 (6 pages).
European Search Report for EP Appln No. 06101498.1, mailed Jun. 20, 2006 (6 pages).
PCT Search Report for PCT Appln No. PCT/US04/25960, mailed Aug. 8, 2006 (10 pages).
PCT Search Report for PCT Appln No. PCT/US2007/012400, mailed Nov. 16, 2007 (13 pages).
Zhang, Guangrong, et al., "Deparaffinization compositions and methods for their use," Reissue U.S. Appl. No. 11/250,142, filed Oct. 13, 2005.
Shi, Shan-Rong, et al., "Enhancement of immunochemical staining in aldehyde-fixed tissue," Reissue U.S. Appl. No. 11/249,180, filed Oct. 11, 2005.
Office Action for Japanese Application No. 2006-34547 dated Dec. 26, 2008 (7 pages).
Office Action for Chinese Application No. 200610007366.7 dated May 8, 2009 (21 pages).
Final Office Action mailed Jan. 19, 2011 for U.S. Appl. No. 11/349,663, 24 pages.
CN Office Action dated Mar. 31, 2011 for Chinese Application No. 200610007366.7, 12 pages.
Sakura Finetek U.S.A., First office action mailed Mar. 31, 2011 for European Application No. 04780745.8, 3 pgs.
Sakura Finetek U.S.A., Third Office Action mailed Jun. 9, 2011 for Chinese Application No. 200610007365.2, 6 pgs.
Sakura Finetek U.S.A., Sixth Office Action mailed Mar. 31, 2011 for Chinese Application No. 200610007366.7, 6 pgs.
Sakura Finetek, Final Office Action mailed Aug. 31, 2011 for U.S. Appl. No. 11/349,663, 20 Pages.
Sakura Finetek U.S.A., Offie Action dated Jun. 9, 2011 for China Application 2006100073652, 6 pages.
Sakura Finetek U.S.A., Japanese office action dated Jul. 6, 2011 for JP Appln. No. 2008-141687.
Sakura Finetek, Non-Final Office Action mailed Jan. 31, 2012 for U.S. Appl. No. 11/349,663., 12 pages.
Sakura Finetek, Final Office Action mailed Mar. 5, 2012 for U.S. Appl. No. 11/349,663., 11 pages.
Sakura Finetek, Japanese Office Action dated Jul. 19, 2012 for Appln. No. 2009-512152.
Sakura Finetek, Office Action mailed Jun. 25, 2012; European Appln No. 07795292.7, 6 pages.
Sakura Finetek, CN Notification of Reexamination dated Sep. 18, 2012 for Chinese Appln. No. 200610007366.7.
Sakura Finetek, Australian Office Action mailed Sep. 21, 2012 for Application No. 2007267881.
Sakura Finetek U.S.A., Inc., Non-Final Office Action dated Oct. 23, 2012 for U.S. Appl. No. 13/018,609.
Sakura Finetek, Non-Final Office Action mailed Jan. 31, 2012 for U.S. Appl. No. 11/349,663.
Sakura Finetek, Australian Office Action mailed Jan. 3, 2012 for 2007267881.
Sakura Finetek, Chinese office action dated Jan. 18, 2012 for CN 200780019204.8.
Sakura Finetek, Japanese Office Action mailed Mar. 1, 2012 for App No. 2008-141687.
Sakura Finetek, Final Office Action mailed Mar. 5, 2012 for U.S. Appl. No. 11/349,663.
Sakura Finetek, Chinese Office Action mailed Feb. 16, 2012 for Chinese App 200610004479.1.
Sakura Finetek, Japanese Office Action mailed Jan. 30, 2012 for Application No. 2009-512152.
Sakura Finetek, Final Office Action mailed May 1, 2012 for U.S. Appl. No. 11/349,663, 13 pages.
Sakura Finetek, Extended Search Report mailed Jun. 4, 2012 for European App No. 12153210.5, 6 pages.
Sakura Finetek, Japanese Office Action mailed Jul. 19, 2012 for Application No. 2009-512152, 2 pages.
Sakura Fineteck U.S.A. Inc., CN Office Action dated May 10, 2010 for Chinese Appln. No. 200610007366.7.
Sakura Finetek U.S.A., Inc., Office Action dated Jul. 21, 2010; Australian Application No. 2008229802.
Sakura Finetek U.S.A., Inc., Office Action dated Aug. 13, 2010; Australian Appln. No. 2006200549.
Sakura Finetek U.S.A., Inc., Office Action mailed Oct. 11, 2010; European Appln No. 07795292.7-1234.

* cited by examiner

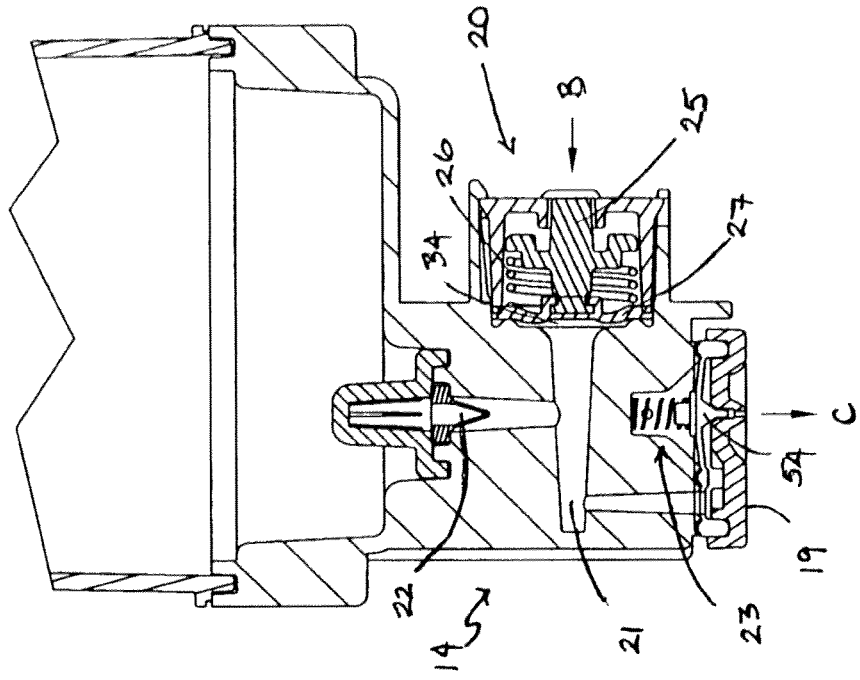
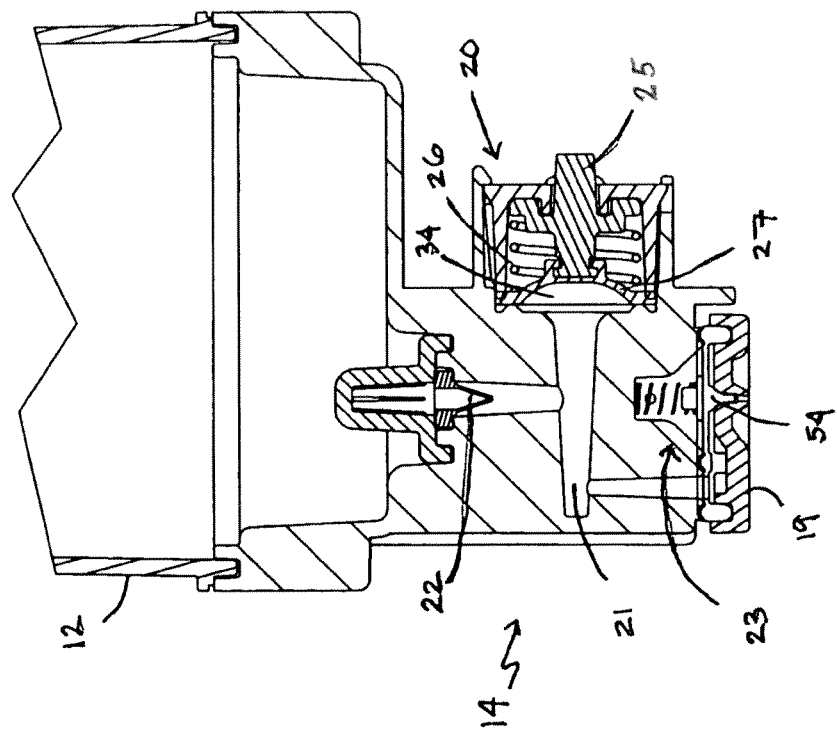

FLUID DISPENSING APPARATUS

FIELD OF THE INVENTION

The present invention relates to biological sample processing systems and in particular to a fluid dispensing apparatus that may be used in a biological sample processing system.

BACKGROUND OF THE INVENTION

While conducting biological tests, it is often necessary to dispense liquids, such as reagents, onto test slides containing tissue specimens. When analyzing tumor tissue for example, a thinly sliced section of the tissue might be placed on a slide and processed through a variety of steps, including dispensing predetermined amounts of liquid reagents onto the tissue. Automated reagent fluid dispensing devices have been developed to precisely apply a sequence of preselected reagents to test slides.

One example of a known reagent dispensing system is illustrated in U.S. Pat. No. 5,232,664 to Krawzak et al. In that system, a reagent dispensing tray can receive plural reagent containers and may include a means for positioning selected reagent containers over slides to receive reagent. An air cylinder or equivalent actuator makes contact with an individual cartridge effecting movement of a spring loaded displacement member. The spring loaded displacement member slides within a cylinder thereby reducing the reagent volume in the cylinder, which in turn causes reagent fluid to be applied over the slides.

One disadvantage associated with such systems is that the dispensing systems often utilize a sliding plunger that is in sealing contact with an internal surface of a cylinder. As a result, the useful life of such systems is limited by wear between the plunger and the cylinder. Systems that include a sliding plunger and cylinder configuration also require precise fitting of the plunger seal so that a fluid seal is maintained between the sliding surfaces during changes in direction of the plunger displacement. In view of these disadvantages, there exists a need for a reagent dispensing system that does not rely upon a sliding seal between a plunger and a cylinder.

An additional disadvantage associated with conventional reagent dispensing systems is the potential misalignment of individual cartridges within mounting apertures of a mounting assembly. In view of this disadvantage, there exists a need for a reagent dispensing system including cartridges that are shaped so as to self align within similarly-shaped mounting apertures.

SUMMARY OF THE INVENTION

The present invention alleviates to a great extent the above-noted and other disadvantages of known fluid dispensing apparatus by providing a fluid dispensing cartridge that can dispense small amounts of fluids accurately without requiring a sliding seal between a sliding plunger and a cylinder.

One aspect of the present invention involves a fluid dispensing cartridge that includes a fluid reservoir and a dispensing assembly that utilizes a deformable member to create a volumetric change in a metering chamber. In one embodiment, the dispensing assembly includes metering components such as a first valve assembly and a second valve assembly that control the flow of fluid into and out of the metering chamber. The deformable member operates with the valve components to meter a desired volume of fluid from the fluid reservoir into the metering chamber, and then to eject the metered fluid from the metering chamber out of the cartridge. The metered fluid may be ejected onto any desired target such as a fluid bath or a slide.

In an embodiment, the metering components operate in conjunction with a pump assembly that is actuated by an external force to deform the deformable member to the eject position, thereby creating a pressure increase within the metering chamber. The increase creates a pressure differential between the metering chamber and the external environment which causes the second valve to open allowing the contents of the metering chamber to be ejected. When the external force is removed from the pump assembly the deformable member is allowed to return to its resting position creating a pressure differential between the reservoir and the metering chamber. That pressure differential causes the first valve to open allowing fluid to flow into the metering chamber from the reservoir.

The deformable member is preferable a diaphragm and a displacement member or piston of the pump assembly is preferably coupled to the diaphragm so that movement of the piston deforms the diaphragm. The deformation of the diaphragm to the eject position causes a reduction of volume in the metering chamber and a resultant increase in pressure. The piston also may be biased by a spring to return the diaphragm to the rest position. An actuator, such as a solenoid, may be positioned outside of the pump assembly adjacent to an exposed portion of the piston so that movement of the solenoid may be used to move the piston.

The fluid dispensing cartridge of the present invention optionally may be used within a fluid dispensing system that includes a plurality of stations at which fluid dispensing cartridges may be located. The stations preferably include mounting apertures that are shaped to receive the cartridges adjacent to a corresponding external actuator assembly. Although the cartridges may rely on gravitational force to seat within their respective mounting apertures, optionally the cartridges are releasably attached to the fluid dispensing apparatus using a mounting assembly. One example of a mounting assembly includes a tab that is located on the cartridge that is received in a slot adjacent to the respective mounting aperture. The tab may be wedge shaped so that as the tab is received by the slot the fit of the tab within the slot becomes tighter.

An additional aspect of the present invention involves a fluid dispensing apparatus including mounting apertures shaped so as to align similarly shaped cartridges, wherein the cartridges and openings have matching cross-sectional profiles. In one embodiment, the cartridges and mounting apertures include matching cross-sectional profiles that only allow the cartridge to mounted in one orientation.

These and other features and advantages of the present invention will be appreciated from review of the following detailed description of the invention, along with the accompanying figures in which like reference numerals refer to like parts throughout.

BRIEF DESCRIPTION OF THE DRAWINGS

FIG. 4 is a cross-sectional view of a portion of the fluid dispensing apparatus of FIG. 1 in a fully closed configuration;

FIG. 5 is a cross-sectional view of a portion of the fluid dispensing apparatus of FIG. 1 in a partially opened configuration;

DETAILED DESCRIPTION OF THE INVENTION

In the following paragraphs, the present invention will be described in detail by way of example with reference to the attached drawings. Throughout this description, the preferred embodiment and examples shown should be considered as exemplars, rather than as limitations on the present invention. As used herein, the "present invention" refers to any one of the embodiments of the invention described herein, and any equivalents. Furthermore, reference to various feature(s) of the "present invention" throughout this document does not mean that all claimed embodiments or methods must include the referenced feature(s).

Figure 2:
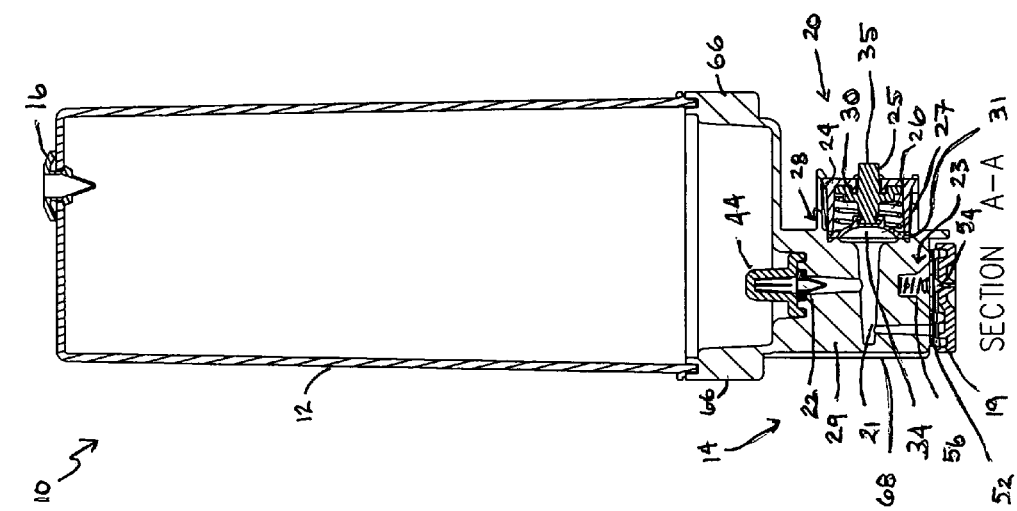
FIG. 2 is a cross-sectional view of the fluid dispensing apparatus of FIG. 1 taken along line A-A.
Figure 1:
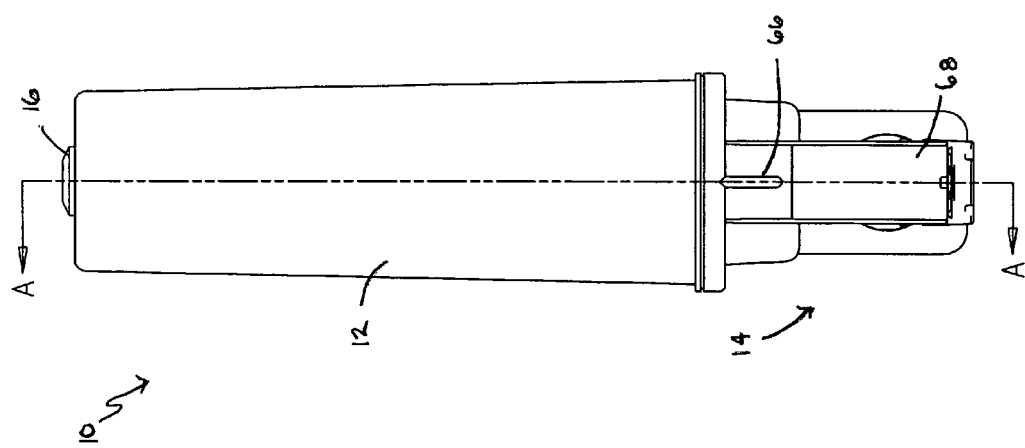
FIG. 1 is a front view of an embodiment of a fluid dispensing apparatus in accordance with the present invention.
Figure 3:
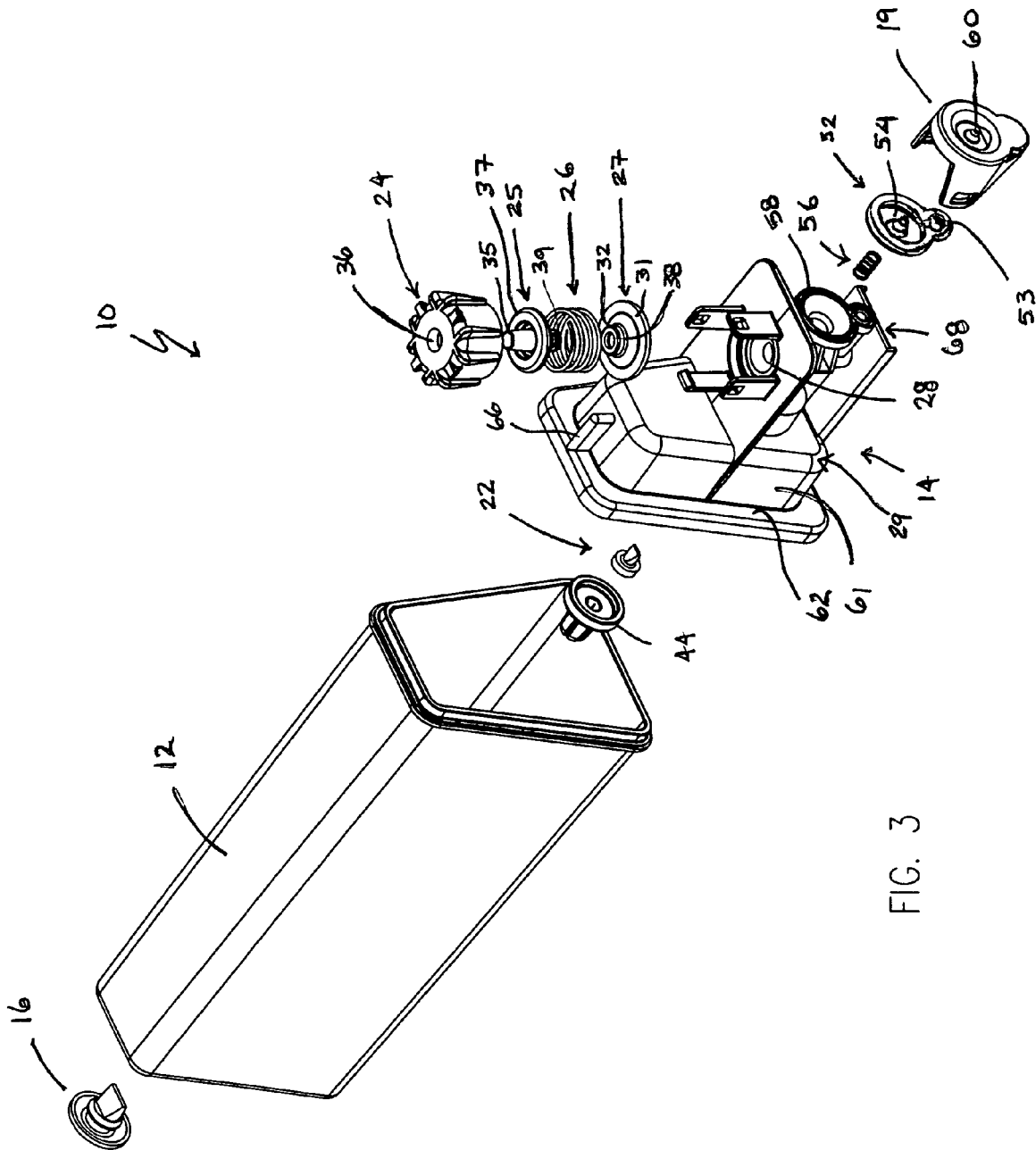
FIG. 3 is an exploded view of the fluid dispensing apparatus of FIG. 1.

FIGS. 1-3 show a preferred embodiment of a fluid dispensing apparatus 10, or cartridge, in accordance with the present invention. Fluid dispensing cartridge 10 generally includes a fluid reservoir 12 that is in fluid communication with a fluid dispensing assembly 14. Fluid reservoir 12 is generally a container that is configured to hold a predetermined amount of a fluid, such as a reagent or a rinsing fluid. Preferably, reservoir 12 is a rigid housing that is constructed from a fluid impermeable material. Fluid reservoir 12 may also include a replaceable fluid bladder or liner (not shown). It should also be appreciated that the reservoir may be constructed from any material suitable for holding liquid such as a chemically inert plastic, for example polyethylene or polypropylene. The reservoir material is preferably gas impermeable to prevent ambient air from contaminating the contents, thereby extending the shelf life of the fluid contained therein. In an embodiment in which a liner or bladder is used, a substantially rigid cover may be included that supports the liner or bladder. Such a rigid cover also may provide a grasping surface for handling and a marking surface so information may be recorded on the cartridge, for example by writing on the surface or affixing a label.

Reservoir 12 includes a pressure valve 16 that allows pressure inside reservoir 12 to equalize to the ambient air pressure. In particular, pressure valve 16 may be used to stabilize pressure within reservoir 12 so that a vacuum is not formed within reservoir 12 after a portion of the contents of reservoir 12 is dispensed through dispensing assembly 14. Pressure valve 16 may be any valve that allows fluid to enter reservoir 12. As shown, pressure valve 16 may be a one-way "duck bill" type check valve. It should be appreciated that any valve may be used for pressure valve 16 such as passive check valves or controlled valves.

Fluid dispensing assembly 14 generally includes a pump assembly 20, a metering chamber 21, a reservoir valve 22, a nozzle valve assembly 23 and a nozzle 19. Pump assembly 20 further includes a moveable pump piston 25, a piston spring 26 and a deformable member, such as diaphragm 27, that are housed between a pump housing 24, or cap, and a portion 28 of a dispensing assembly housing 29. Portion 28 of dispensing assembly housing 29 and pump housing 24 are configured to be coupled together aid to collectively define a pump cavity 30 that houses piston 25, piston spring 26 and diaphragm 27. In the present embodiment, pump housing 24 held in place by a plurality of tabs that extend from dispensing assembly housing 29 so that pump housing 24 ma be snapped into place with diaphragm 27 interposed between housing 24 and housing 29. It should be appreciated that pump housing 24 may be coupled to dispensing assembly housing 29 by any mechanism known in the art for example, housing 24 may be adhered or welded to housing 29.

Diaphragm 27 is a substantially flexible member that may be deformed between a rest position and an eject position. Diaphragm 27 includes a first mounting portion 31 that is configured to be coupled to portion 28 of dispensing assembly housing 29 and a second mounting portion 32 that is configured to mount to an interior end 33 of piston 25. As shown in FIG. 2, diaphragm 27 is in the rest position, in which it is generally bowl-shaped. In the rest position, the concave interior surface of diaphragm 27 defines a displacement space 34, which forms part of metering chamber 21. Preferably, first mounting portion 31 of diaphragm 27 is fixedly coupled and fluidly sealed to portion 28 of dispensing assembly housing 29 so that fluid within metering chamber 21 is prevented from flowing past diaphragm 27 toward piston 25. As will be described in further detail below, because first mounting portion 31 is stationary with respect to dispensing assembly housing 29 and metering chamber 21, and diaphragm 27 is deformable, pump assembly 20 does not require a sliding fluid seal to create pressure changes within metering chamber 21.

Pump piston 25 is slidably housed within pump housing 24. A portion of piston 25 extends out of pump housing 24 so that a force may be applied to the external portion of piston 25 to actuate dispensing assembly 14. Interior end 33 of pump piston 25 is coupled to second mounting portion 32 of diaphragm 27. Piston 25 and diaphragm 27 are coupled so that second mounting portion 32 of diaphragm 27 translates with translation of piston 25. Diaphragm 27 and piston 25 may be coupled. As shown, second mounting portion 32 of diaphragm 27 includes an annular flange 38 that is received within a circumferential channel 39 of piston 25. Circumferential channel 39 is located substantially adjacent to interior end 33 of piston 25.

The external portion of piston 25 includes an exterior end 35 that extends from pump cavity 30 through an aperture 36 of pump housing 24. In the present embodiment, the length between interior end 33 and exterior end 35 of piston 25 is selected so that exterior end 35 remains exposed when diaphragm 27 is moved between the rest position and the eject position (shown in FIG. 5 and described below). Exterior end 35 of piston 25 provides a surface for external forces to be applied to piston 25 to move diaphragm 27 between the rest position and the eject position.

Spring 26 may be used to position piston 25 when there is no external force applied to piston 25. Spring 26 is interposed between first mounting portion 31 of diaphragm 27 and a spring contact flange 37 of piston 25. In the illustrated embodiment, spring 26 is configured so that it is under compression and biases piston 25 away from pump portion 28 of dispensing assembly housing 29 so that diaphragm 27 is in a rest position. It should be appreciated that spring 26 may be configured to bias piston 25 in any desired direction. It should further be appreciated that spring 26 may be replaced by a plurality of spring members if desired. It should also be appreciated that diaphragm 27 may be configured to provide the spring force to bias piston 25 into a desired position. It should be further appreciated that piston 25 and spring 26 may be omitted so that external force is applied directly to diaphragm 27.

Metering chamber 21 is a cavity configured to hold liquid that is located between reservoir valve 22, diaphragm 27 and nozzle valve assembly 23. Metering chamber 21 provides a holding space for a predetermined volume of fluid that has flown from reservoir 12 into dispensing assembly 14 prior to being ejected from cartridge 10. Metering chamber 21 may be any desired size or shape. Preferably, metering chamber 21 has a volume that closely approximates the volume dispensed during each dispensing cycle of cartridge 10.

The flow of fluid from reservoir 12 into metering chamber 21 is regulated by reservoir valve 22, which is located generally between metering chamber 21 and reservoir 12. In the present embodiment, reservoir valve 22 is a passive, one-way "duck bill" check valve. The deformable flaps of the duck bill valve seal against each other when the valve is closed and separate from each other to form a gap when the valve is opened.

The properties of reservoir valve 22 are chosen so that it allows fluid communication between reservoir 12 and metering chamber 21 when a desired pressure differential between reservoir 12 and metering chamber 21 is created. As described in further detail below, actuation of pump assembly 20 is used to alter the fluid pressure within metering chamber 21 so that the fluid pressure in metering chamber 21 differs from the fluid pressure of reservoir 12 and the ambient environment. In the present embodiment, valve 22 is configured to be closed when there is minimal or no difference in pressure between reservoir 12 and metering chamber 21 or when the pressure in reservoir 12 is less than the pressure in metering chamber 21. When the pressure inside reservoir 12 exceeds the fluid pressure in metering chamber 21 by a selected threshold difference, reservoir valve 22 opens. It should be appreciated that reservoir valve 22 may be any passive or active valve known in the art. Such active valves include solenoid valves and any other actively controlled valve known in the art and the position of the active valve may be automatically or manually controlled through a valve controller.

An optional filter 44 is included adjacent reservoir valve 22. Filter 44 is configured to filter fluid before it flows into reservoir valve 22 from reservoir 12. As shown, filter 44 is a cap that includes narrow slots that are sized to prevent debris from flowing into reservoir valve 22 and filter 44 retains reservoir valve 22 in housing 29. However, it should be appreciated that any filter device may be used such as, for example, a filter made of mesh or foam.

Nozzle valve assembly 23 is used to regulate the flow from metering chamber 21 out of cartridge 10. Nozzle valve assembly 23 is generally located between metering chamber 21 and nozzle 19. In the present embodiment, nozzle valve assembly 23 is a passive valve that includes a diaphragm 52 and a valve spring 56. Diaphragm 52 is a flexible member that includes a pass-through aperture 53 and a peak 54 and is interposed between dispensing assembly housing 29 and nozzle 19. The perimeter of diaphragm 52 is coupled to a sealing surface 58 included on dispensing assembly housing 29 so that fluid within metering chamber 21 is prevented from flowing between sealing surface 58 and diaphragm 52. Pass-through aperture 53 is aligned with a portion of metering chamber 21 so that fluid may flow from metering chamber 21 past diaphragm 52 and into a valve chamber 57, which is a volume defined by the lower surface of diaphragm 52 and the top surface of nozzle 19.

Peak 54 is a cone-shaped protrusion that extends from a surface of diaphragm 52 in the direction of nozzle 19. When fluid dispensing apparatus 14 is in either a resting or filling state, described in greater detail below, peak 54 extends at least partially into a nozzle fluid conduit 60 so that the outer surface of peak 54 seals against the surface of fluid conduit 60. The location of sealing between peak 54 and nozzle 19 is preferably within conduit 60 so that the volume of space between the seal and the outlet of conduit 60 is minimized. Minimizing that volume reduces the likelihood of evaporation of liquid in that space which could cause conduit 60 to become clogged. It should be appreciated that peak 54 may be configured in any way suitable to seal against the surface of conduit 60. For example, if fluid conduit 60 has a square cross-sectional shape, peak 54 may likewise be constructed with a square cross-section such as by creating peak 54 in the shape of a pyramid or a truncated pyramid.

Spring 56 is located in a cavity 68 that is defined by dispensing assembly housing 29 and diaphragm 52 and an aperture 69 is provided so air can escape from cavity 68 during compression of spring 56. Preferably, spring 56 is placed under compression so that it biases peak 54 into conduit 60 when the fluid pressure within metering chamber is at or near ambient pressure and is selected to prevent dripping when the fluid is at that pressure. However, spring 56 is also selected so that a fluid pressure increase within metering chamber 21 and valve chamber 57 caused by actuation of pump assembly 20 will cause at least a portion of diaphragm 52 to be moved upward toward dispensing assembly housing 29 against the biasing force of spring 56. Peak 54 moves with diaphragm 52 away from nozzle 19, which removes the fluid seal between peak 54 and conduit 60. As a result, pressurized fluid becomes free to flow through conduit 60 of nozzle 19 past peak 54.

The properties of diaphragm 52 and spring 56 are chosen so that nozzle valve assembly 23 allows fluid communication between metering chamber 21 and fluid conduit 60 of nozzle 19 when a desired pressure differential between metering chamber 21 and the external environment is created. In the present embodiment, spring 56 is configured to hold diaphragm 52 in a closed position (i.e., there is no fluid communication between metering chamber 21 and conduit 60) when there is minimal or no difference in pressure between metering chamber 21 and the environment. As described in further detail below, actuation of pump assembly 20 alters the fluid pressure within metering chamber 21 and valve chamber 57 so that the pressure differs from the fluid pressure of the external environment. When the force acting upon diaphragm 52 from the fluid within nozzle valve chamber 57 exceeds the force acting upon diaphragm 52 from spring 56, diaphragm 52 is moved upward so that a gap is formed between the outer surface of diaphragm peak 54 and the inner surface of conduit 60. As a result, fluid is permitted to flow from metering chamber 21 through conduit 60. Furthermore, it should be appreciated that an active valve may be used, such as a solenoid or other active valve and the position of the active valve may be controlled automatically or manually through a valve controller. Similar to reservoir valve assembly 22, nozzle valve assembly 23 may be any passive or actively controlled valve known in the art.

The configuration of nozzle 19 and conduit 60 may be selected to create any desired flow attributes out of cartridge 10. For example, dispensing assembly 14 may be configured to provide a directed stream of fluid, a wide fluid spray or fluid droplets. It should be appreciated that the flow attributes of the pressurized fluid through nozzle 19 may selected as desired by selecting the shape of fluid conduit 60 and by tailoring pump assembly 20 to create a desired pressure increase within metering chamber 21. Nozzle 19 may be made of any material and is preferably constructed from a chemically inert hydrophobic hard plastic material so that a last drop of liquid may be prevented after ejection. In addition, as shown in FIG. 3, nozzle may be coupled directly to dispensing assembly housing 29 by tabs so that nozzle 19 is snapped into place. It should be appreciated that nozzle 19 may alternatively, or additionally, be mechanically coupled to dispensing assembly housing 29 by adhesive and/or welding. It should further be appreciated that nozzle may be coupled to fluid dispensing housing 29 through diaphragm 52.

After cartridge 10 is assembled, reservoir 12 may be filled with a reagent or other liquid as desired. Generally, immediately after the initial filling of reservoir 12, metering chamber 21 is substantially empty. In order to prepare cartridge 10 for use, dispensing assembly 14 may be primed by actuating pump assembly 20. As will be appreciated from the description below, actuating pump assembly 20 causes the fluid pressure within metering chamber 21 to increase which causes the contents of metering chamber 21 to be ejected through nozzle 19. During priming, the air that initially occupies metering chamber 21 is ejected and replaced by liquid from reservoir 12.

Figure 6:
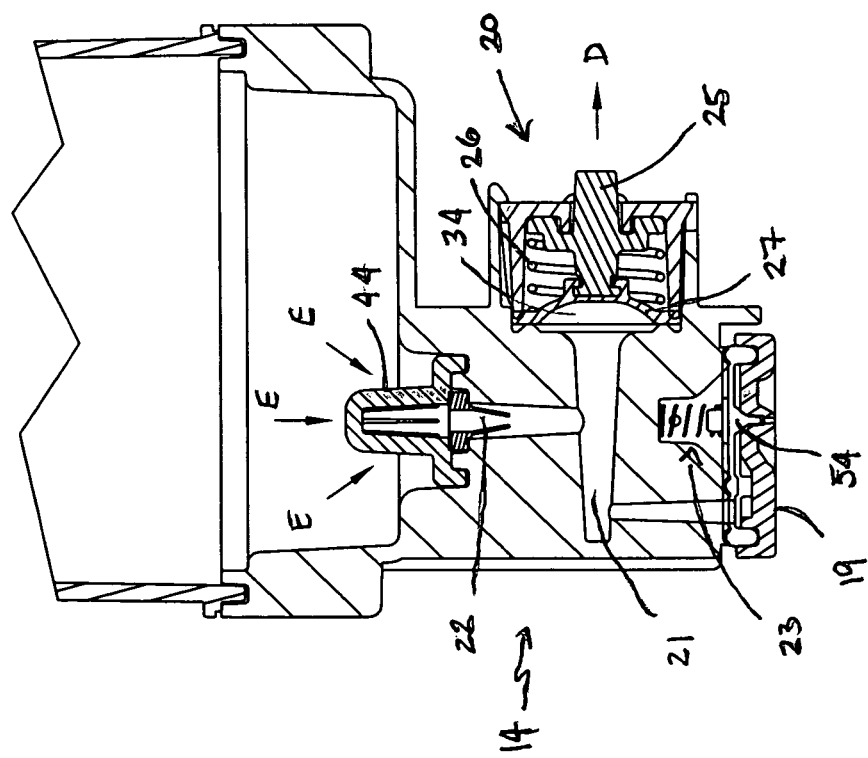
FIG. 6 is another cross-sectional view of a portion of the fluid dispensing apparatus of FIG. 1 in a partially opened configuration.

Referring to FIGS. 4-6 operation of fluid dispensing assembly 14 will be described. During operation, fluid dispensing assembly 14 is configured in one of a resting state (i.e., fully closed), an ejecting state (i.e., partially opened with the nozzle valve opened) or a filling state (i.e., partially opened with the reservoir valve opened). Dispensing assembly 14 is in a resting state when no external force is applied to piston 25 of pump assembly 20. In that state, reservoir valve 22 and nozzle valve assembly 23 are closed, and there is no fluid flow either into dispensing assembly 14 from reservoir 12 or out of dispensing assembly 14 from metering chamber 21. In addition, diaphragm 27 is in the rest position, displacement space 34 has a maximum volume and spring 26 is under compression so that it urges piston 25 away from metering chamber 21. In the present embodiment, when dispensing assembly 14 is in the resting state, the fluid pressure within reservoir 12 and metering chamber 21 are approximately equalized with the external fluid pressure.

Referring to FIG. 5, dispensing assembly 14 may be placed in the ejecting state by applying an external force to piston 25 that is sufficient to overcome the force exerted on piston 25 by spring 26. The force causes piston 25 to move in the direction of arrow B. Movement of piston 25 in the direction of arrow B causes diaphragm 27 to be deformed and transforms it from the bowl-shaped rest position, shown in FIG. 4, into the substantially flat eject position, shown in FIG. 5. Deformation of diaphragm 27 reduces the volume of displacement space 34 and metering chamber 21, which increases the fluid pressure within metering chamber 21. Reservoir valve 22 remains closed in response to the increase in fluid pressure within metering chamber 21. Nozzle valve assembly 23, however, is configured to open when there is a sufficient increase in fluid pressure within metering chamber 21. As a result, the pressurized fluid within metering chamber 21 is ejected through nozzle 19, as shown by arrow C.

Referring to FIG. 6, after the external force on piston 25 is removed, dispensing assembly 14 enters the filling state. During ejection, piston 25 is translated and spring 26 is compressed in reaction to the external force. Upon removal of the external force, the compression force of spring 26 causes piston 25 to translate away from metering chamber 21 in the direction of arrow D. The movement of piston 25 in that direction causes diaphragm 27 to transform from the eject position to the rest position. That deformation results in an increase in the volume of displacement space 34, which creates a partial vacuum (i.e., a reduction in pressure within metering chamber 21 below the fluid pressure in reservoir 12 and the external pressure) within metering chamber 21. The partial vacuum causes reservoir valve 22 to open when a sufficient pressure differential is achieved, and fluid is permitted to flow from reservoir 12 into metering chamber 21, as shown by arrows E. At the same time, nozzle valve assembly 23 closes because the combined force placed on diaphragm 52 by spring 56 is greater than the force caused by the fluid pressure of the environment on diaphragm 52. In this configuration, fluid is allowed to flow from reservoir 12 into metering chamber 21 until the pressure within metering chamber 21 is substantially equal to the fluid pressure within reservoir 12. When the pressure within metering chamber 21 is substantially equal to the fluid pressure within reservoir 12, reservoir valve 22 closes.

Figure 8:
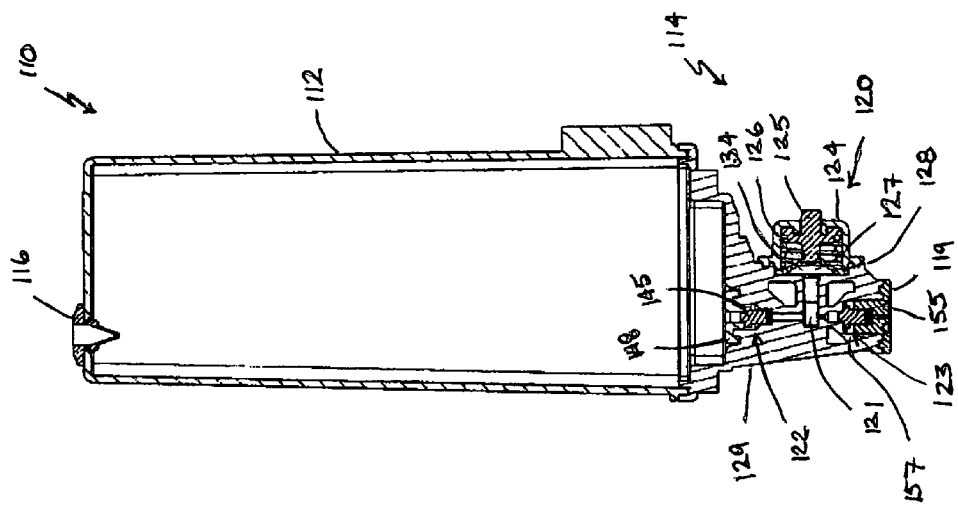
FIG. 8 is a cross-sectional view of the fluid dispensing apparatus of FIG. 7 taken along line E-E.
Figure 7:
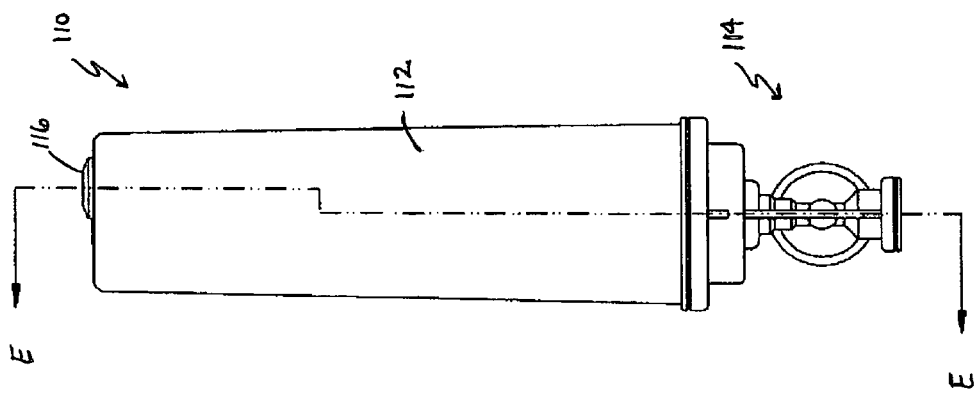
FIG. 7 is a front view of an embodiment of a fluid dispensing apparatus in accordance with the present invention.
Figure 9:
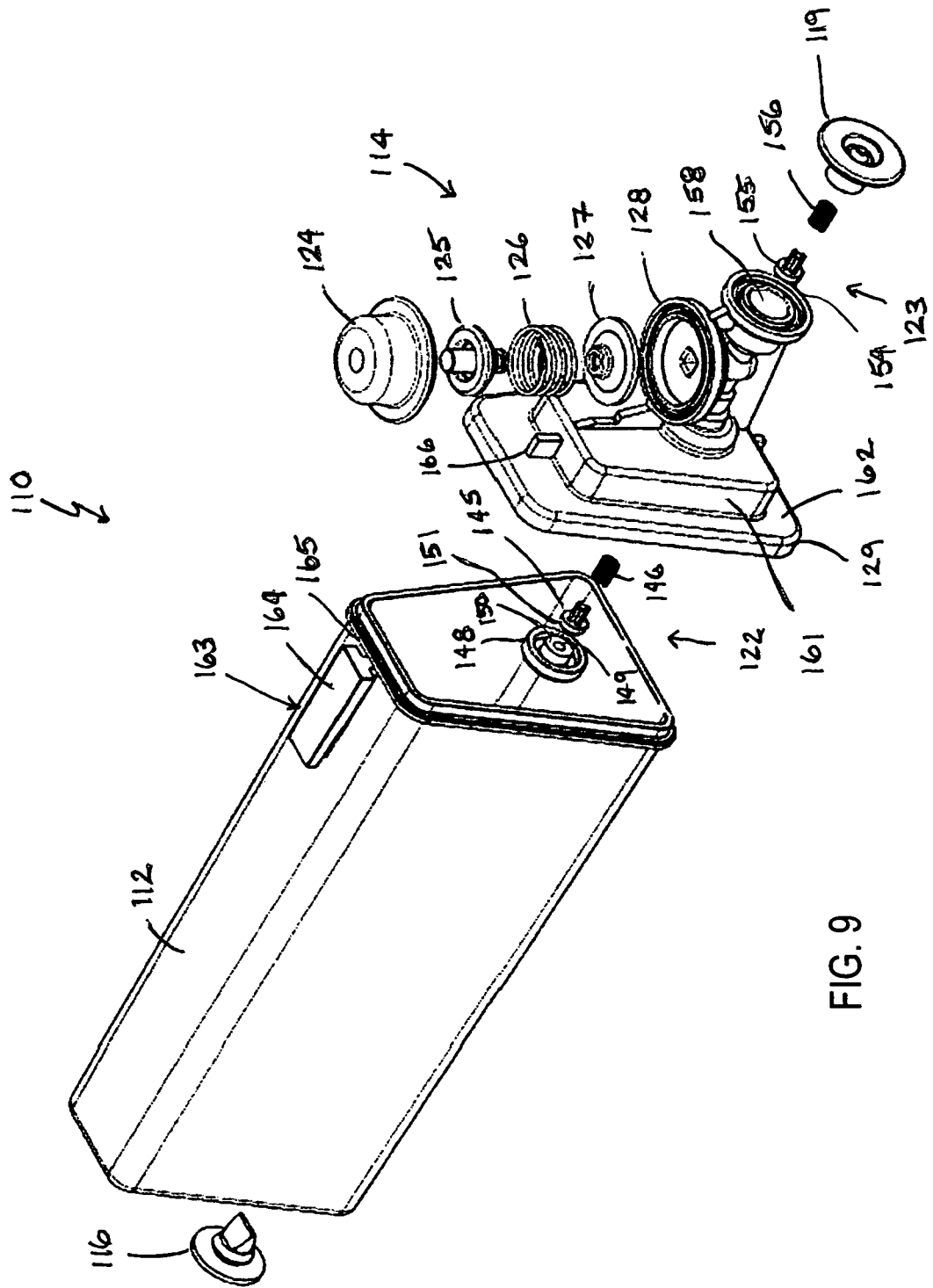
FIG. 9 is an exploded view of the fluid dispensing apparatus of FIG. 7.

FIGS. 7-8 show another embodiment of a fluid dispensing cartridge in accordance with the present invention. It should be appreciated that fluid dispensing cartridge 110 uses similar or identical components to the embodiment previously described and such components are indicated by similar reference numbers. Fluid dispensing cartridge 110 generally includes a fluid reservoir 112 and a fluid dispensing assembly 114 that is in communication with fluid reservoir 112. Fluid reservoir 112 is generally a container that is configured to hold a predetermined amount of a fluid, such as a reagent or a rinsing fluid. It should be appreciated that fluid reservoir 112 may be constructed as described above with respect to the previous embodiment.

Reservoir 112 also includes a pressure valve 116 that allows fluid to enter reservoirs 112 and used to stabilize pressure within reservoir 112 so that a vacuum is not formed within reservoir 112 after a portion of the contents of reservoir 112 is dispensed through dispensing assembly 114.

Fluid dispensing assembly 114 generally includes a pump assembly 120, a metering chamber 121, a reservoir valve assembly 122, a nozzle valve assembly 123 and a nozzle 119. With the exception of reservoir valve assembly 122, nozzle valve assembly 123 and nozzle 119, the components of fluid dispensing assembly 114 are similar to those described above and will not be described again in full detail. Pump assembly 120 includes a moveable pump piston 125, a piston spring 126 and a diaphragm 127, that are housed between a pump housing 124 and a portion 128 of a dispensing assembly housing 129.

Diaphragm 127 is a substantially flexible member that may be deformed between a rest position and an eject position. As shown in FIG. 2, diaphragm 127 is in the rest position, in which it is generally shaped as a concave bowl and defines a displacement space 134, which forms part of metering chamber 121.

Pump piston 125 is slidably housed within pump housing 124 and a portion of piston 125 extends out of pump housing 124 so that a force may be applied to the external portion of piston 125 to actuate dispensing assembly 114. Piston 125 and diaphragm 127 are coupled so that a portion of diaphragm 127 translates with translation of piston 125. Spring 126 positions piston 125 away from metering chamber 121 when there is no external force applied to piston 125, which places diaphragm 127 is in a rest position.

Metering chamber 121 is a fluid chamber that is located between reservoir valve assembly 122, diaphragm 127 and nozzle valve assembly 123. Metering chamber 121 provides a holding space for a predetermined volume of fluid that has flown from reservoir 112 prior to being ejected from cartridge 110.

Reservoir valve assembly 122 regulates the flow of fluid from reservoir 112 into metering chamber 121 and valve assembly 122 is located generally between metering chamber 121 and reservoir 112. In the present embodiment, reservoir valve assembly 122 is a passive, one-way check valve that includes a piston 145 and a piston spring 146. Piston 145 is movable between a sealing position and an opened position and piston spring 146 biases piston 145 into the sealing position.

Piston 145 and piston spring 146 are mounted within a reservoir valve chamber 147 that is collectively defined by dispensing assembly housing 129 and a reservoir valve cap 148. Cap 148 includes a reagent conduit 149 that is configured to provide fluid communication between reservoir 112 and metering chamber 121 when piston 145 is in the opened position. Cap 148 includes a sealing surface 150 that is configured to selectively abut a sealing surface 151 on valve piston 145 when it is in the sealing position to prevent fluid communication between reservoir 112 and metering chamber 121. It should be appreciated that reservoir valve assembly 122 may be any passive or active (i.e., actively controlled) valve known in the art.

The properties of spring 146 are chosen so that reservoir valve assembly 122 allows fluid communication between reservoir 112 and metering chamber 121 when a desired pressure differential between reservoir 112 and metering chamber 121 is created. In the present embodiment, spring 126 is configured to bias piston 145 into the sealing position (i.e., there is no fluid communication between reservoir 112 and metering chamber 121) when there is minimal or no difference in pressure between reservoir 112 and metering chamber 121 or when the pressure in reservoir 112 is less than the pressure in metering chamber 121. As described in further detail below, actuation of pump assembly 20 may be used to alter the fluid pressure within metering chamber 121 so that the fluid pressure in metering chamber 121 may differ from the fluid pressure of reservoir 112. When the combined force on piston 145 caused by spring 126 and the fluid pressure within metering chamber 121 is lower than the force exerted on piston 145 from the fluid pressure within reservoir 112 piston 145 is moved downward, toward metering chamber 121 so that a gap is formed between sealing surface 150 and sealing surface 151. As a result, fluid is permitted to flow from reservoir 112 into metering chamber 121. In particular, when the pressure inside reservoir 112 exceeds the fluid pressure in metering chamber 121 by a selected threshold difference reservoir valve assembly 122 opens. It should be appreciated that piston 145 of reservoir valve assembly 122 may be replaced by a ball or any other member that includes a surface that may seal against a sealing surface 150 of the valve cap. Furthermore, is should be appreciated that an active valve may be used, such as a solenoid or other actively controlled valve and the position of the active valve may be automatically or manually controlled through a valve controller.

Nozzle valve assembly 123 regulates the flow of fluid from metering chamber 121 and out of cartridge 110 through nozzle 119. Nozzle valve assembly 123 is generally located between metering chamber 121 and nozzle 119. Similar to reservoir valve assembly 122, nozzle valve assembly 123 may be any passive or actively controlled valve known in the art. In the present embodiment, nozzle valve assembly 123 is a passive, one-way check valve that includes a valve piston 155 and a valve spring 156 that are housed within a nozzle valve chamber 157 collectively defined by dispensing assembly housing 129 and nozzle 119. A sealing surface 158 is included on dispensing assembly housing 129 adjacent to piston 155 that is configured to selectively abut against a sealing surface 159 included on an upper end of piston 155.

The properties of spring 156 are chosen so that nozzle valve assembly 123 allows fluid communication between metering chamber 121 and a fluid conduit 160 of nozzle 119 when a desired pressure differential between metering chamber 121 and the external environment is created. In the present embodiment, spring 156 is configured to be in a closed position (i.e., there is no fluid communication between metering chamber 121 and conduit 160) when there is minimal or no difference in pressure between metering chamber 121 and the environment or when the external pressure is greater than the pressure in metering chamber 121. Actuation of pump assembly 120 alters the fluid pressure within metering chamber 121 so that the pressure within metering chamber 121 differs from the fluid pressure of the external environment. When the combined force on piston 155, caused by spring 156 and the external pressure, is lower that the force exerted on piston 155 from the fluid pressure within metering chamber 121, piston 155 is caused to move downward toward nozzle 119 so that a gap is formed between sealing surface 158 and sealing surface 159. As a result, fluid is permitted to flow from metering chamber 121 through conduit 160 of nozzle 119. It should be appreciated that an active valve may be used, such as a solenoid or other active valve and the position of the active valve may be controlled automatically or manually through a valve controller.

Figure 11:
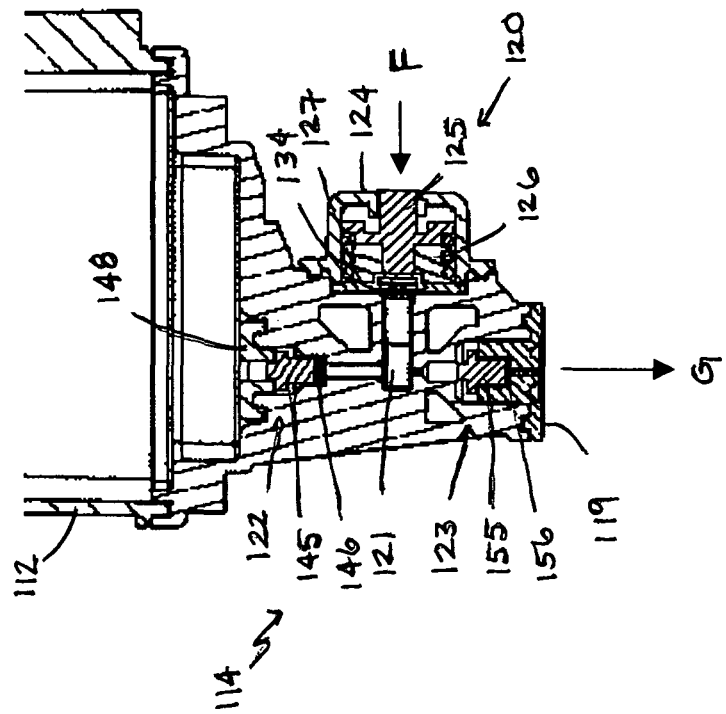
FIG. 11 is a cross-sectional view of a portion of the fluid dispensing apparatus of FIG. 7 in a partially opened configuration.
Figure 10:
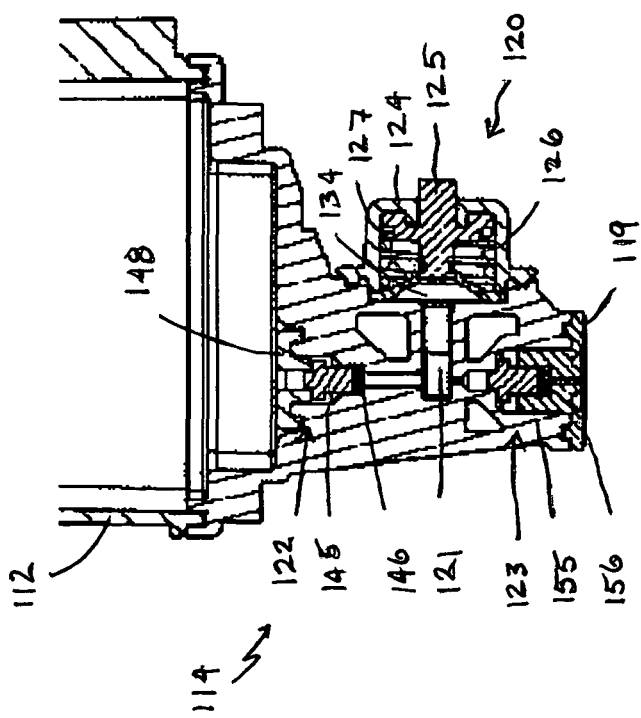
FIG. 10 is a cross-sectional view of a portion of the fluid dispensing apparatus of FIG. 7 in a fully closed configuration.
Figure 12:
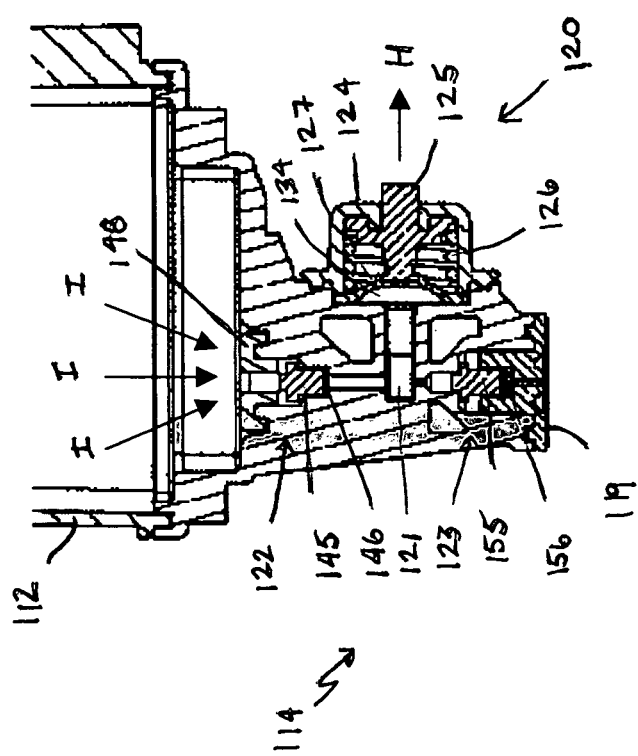
FIG. 12 is another cross-sectional view of a portion of the fluid dispensing apparatus of FIG. 7 in a partially opened configuration.

Operation of fluid dispensing assembly 114 is illustrated by FIGS. 10-12. Similar to the previously described embodiment, fluid dispensing assembly 114 is configured in one of a resting state, an ejection state, or a filling state duing operation. Reservoir valve assembly 122 and nozzle valve assembly 123 are closed when dispensing assembly 114 is in the resting state, shown in FIG. 10. As a result, there is no fluid flow either into dispensing assembly 114 from reservoir 112 or out of dispensing assembly 114 from metering chamber 121. In that state, diaphragm 127 is in the rest position and displacement space 134 has a maximum volume. In addition, spring 126 is under compression so that piston 125 is urged away from metering chamber 121.

Referring to FIG. 11, dispensing assembly 114 is placed in the ejection state by applying an external force to piston 125. The force causes piston 125 to move in the direction of arrow F. Movement of piston 125 in the direction of arrow F causes diaphragm 127 to be deformed into the substantially flat eject position. Deformation of diaphragm 127 reduces the volume of displacement space 134 and metering chamber 121, which increases the fluid pressure within metering chamber 121. Reservoir valve assembly 122 remains closed in response to the increase in fluid pressure within metering chamber 121, but nozzle valve assembly 123 is configured to open when there is a sufficient increase in fluid pressure within metering chamber 121. As a result, the pressurized fluid within metering chamber 121 is ejected through nozzle 119, as shown by arrow G.

After the external force is removed from piston 125, dispensing assembly 114 enters the filling state, shown in FIG. 12. Upon removal of the external force the compression force of spring 126 causes piston 125 to translate away from metering chamber 121 in the direction of arrow H, which causes diaphragm 127 to transform from the eject position to the rest position. That deformation results in an increase in the volume of displacement space 134, which creates a partial vacuum within metering chamber 121. That vacuum causes reservoir valve assembly 122 to open when a sufficient pressure differential is achieved, and fluid is permitted to flow from reservoir 112 into metering chamber 121, as shown by arrows I. At the same time, nozzle valve assembly 123 closes because the combined force placed on piston 150 by external fluid pressure and spring 156 is greater than the force caused by the fluid pressure within metering chamber 121 on piston 155. In this configuration, fluid is allowed to flow from reservoir 112 into metering chamber 121 until the pressure within metering chamber 121 is substantially equal to the fluid pressure within reservoir 112. When the pressure within metering chamber 121 is substantially equal to the fluid pressure within reservoir 112 reservoir valve assembly 122 closes under the influence of spring 146.

Fluid dispensing cartridges also can be used in connection with a larger fluid dispensing system, such as that described below with respect to FIGS. 13 and 14. In particular, cartridge 10 optionally includes an alignment surface 61 and a shoulder 62 and cartridge 110 includes an alignment surface 161 and a shoulder 162 that are useful for properly orienting the cartridge within the system. As will be described in further detail below, the respective alignment surface interfaces with an aperture in the system so that the fluid conduit of the respective nozzle may be easily aligned with a desired fluid dispensing target. Furthermore, the shoulder may be used to control the distance between the nozzle and the fluid dispensing target. Cartridges 10 and 110 may be manufactured (i.e., machined or molded) so that the respective alignment surfaces and shoulders have low tolerances for accurate alignment of the cartridge within a larger dispensing system. Additional mounting and/or alignment features may also be included on the cartridges. For example, cartridge 10 also includes an alignment surface 68 that is configured to abut a portion of a dispensing system. In addition, cartridge 110 optionally includes a mounting tab 163 that will be described in greater detail below in relation to FIGS. 15 and 16. It should be understood that any form of alignment assisting features may be used that can assist with positioning the cartridge as desired for use in the respective fluid dispensing system.

Figure 13:
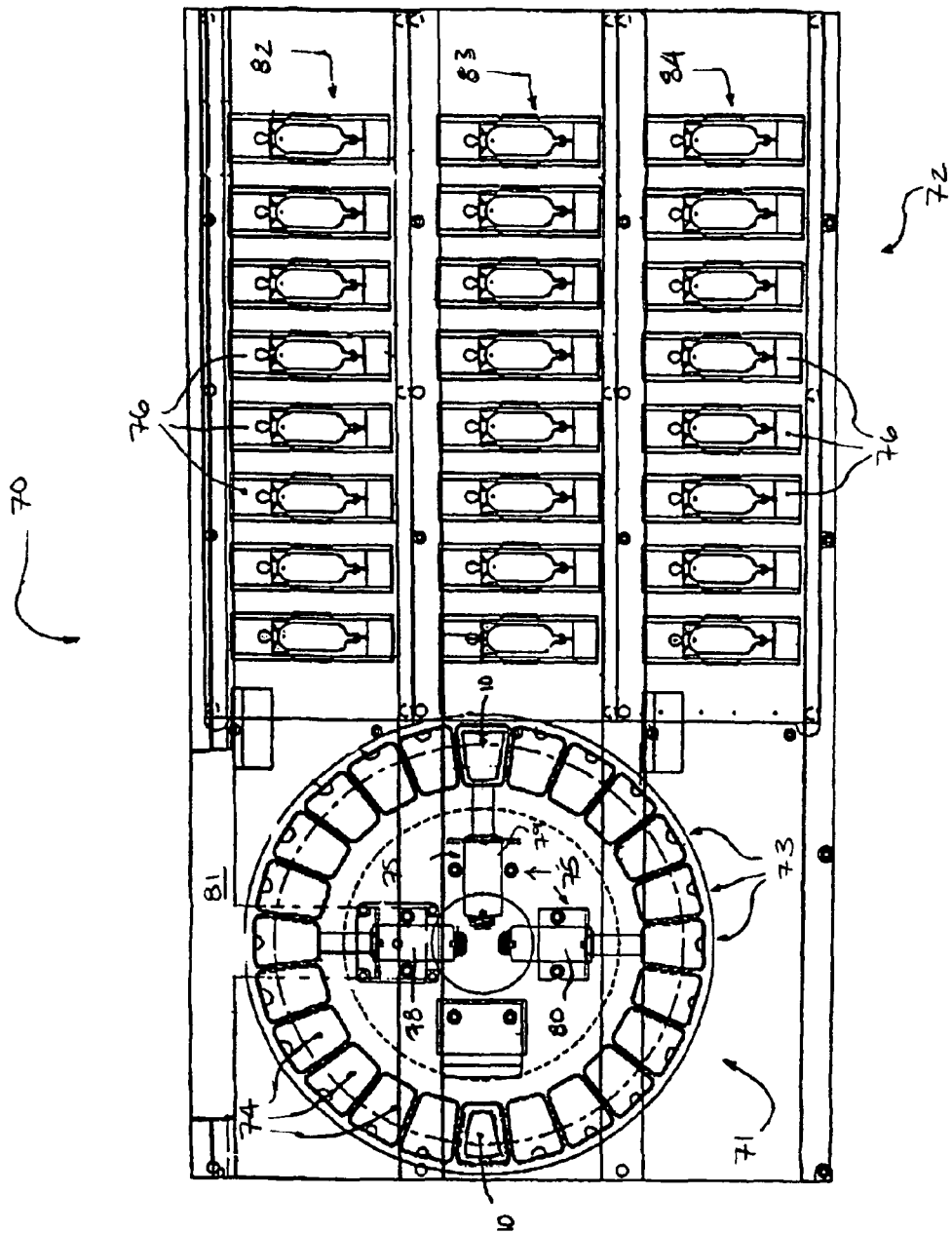
FIG. 13 is a top view of a fluid dispensing system in which a fluid dispensing apparatus in accordance with the present invention may be used.
Figure 14:
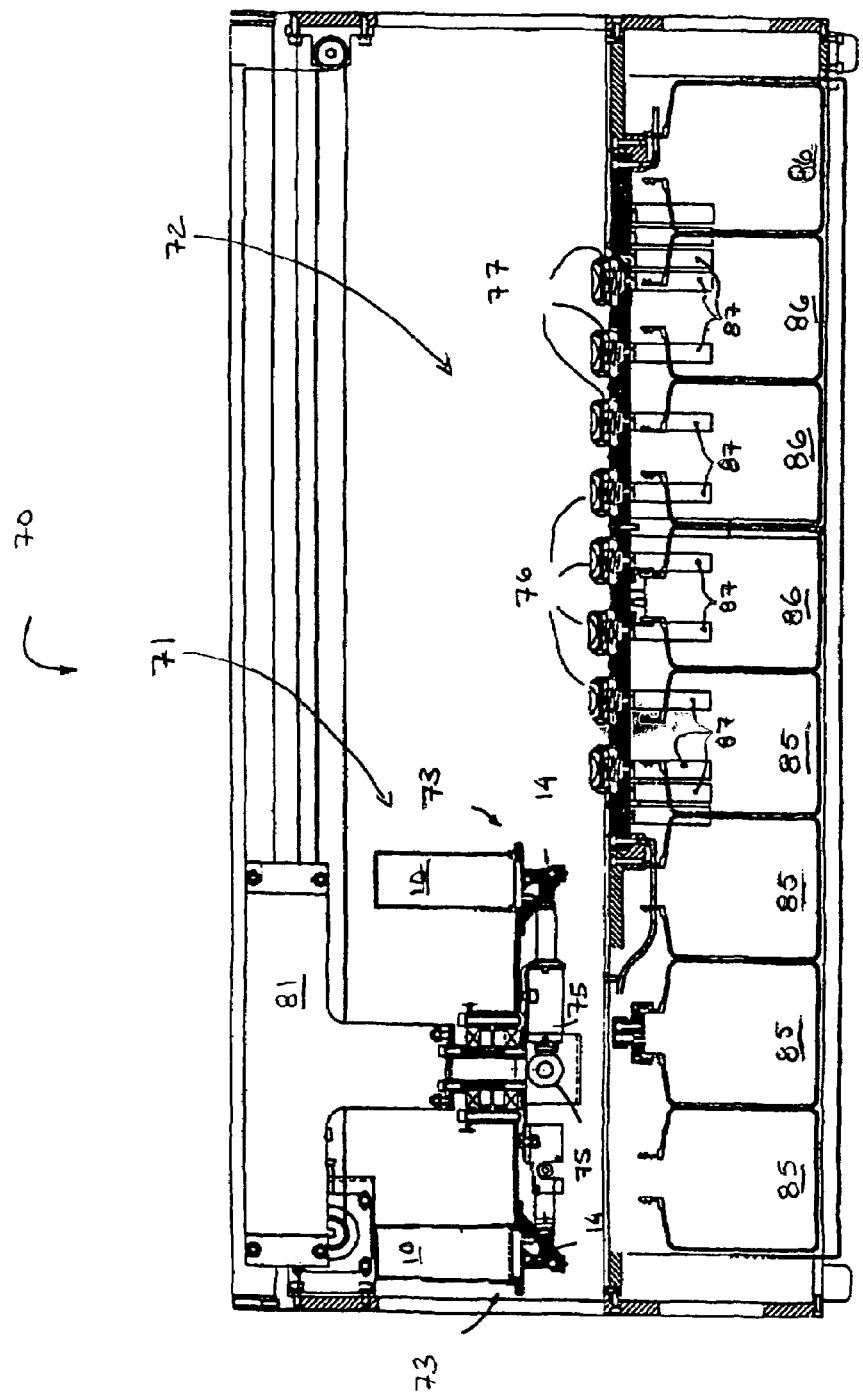
FIG. 14 is a side cross-sectional view of the fluid dispensing system of FIG. 13.

FIGS. 13 and 14 show an exemplary embodiment of a fluid dispensing system 70 that incorporates one or more fluid dispensing cartridges according to the present invention. System 70 generally includes a cartridge mounting assembly 71 and a sample support assembly 72. Cartridge mounting assembly 71 includes a plurality of stations 73 at which fluid dispensing cartridges 10 are mounted. Stations 73 preferably include mounting apertures 74 that are configured to receive and position the fluid dispensing cartridges adjacent to an actuator assembly 75. It should be understood that any form of fluid dispensing system 70 may be used that can receive the cartridge and actuate the dispensing assembly to dispense reagents as desired.

Fluid dispensing system 70 also includes a plurality of receiving members 76 mounted on sample support assembly 72. Receiving members 76 may be any item upon which it is desired to dispense fluids from cartridges 10. Examples of suitable receiving members 76 include slide retaining trays, sample containers and mixing baths. Preferably, receiving members 76 are microscope slide retaining trays holding slides that have tissue samples positioned on them, wherein the slides are positioned face down on the respective tray 76. In such a system the reagent from a fluid dispensing apparatus 10 is not dispensed onto the slide or the sample it contains, but rather is dispensed onto a receiving surface of the slide tray 76 and optionally flows such as via vacuum induced pressure differentials or capillary action underneath the slide that is positioned on the slide tray 76. Optionally, receiving members 76 may be mounted on heating pads 77 that are configured to provide selective heating of the slides or other portions of receiving members 76. Heating pads 77 may optionally be spring-loaded to improve contact between receiving members 76 and one or more of heating pads 77.

Receiving member support assembly 72 is positioned generally below cartridge mounting assembly 71 so that gravity may be used to deliver fluids from cartridges 10 to receiving members 76 as described above. Preferably, cartridge mounting assembly 71 is movable with respect to the stationary receiving member support assembly 72 so that cartridges 10 may be positioned to dispense fluids on any desired receiving member 76. In an alternative embodiment, both cartridge mounting assembly 71 and sample support assembly 72 are movable relative to one another so dispensing fluids is achieved by moving both relative to one another. As shown in FIG. 13, the receiving members 76 may all be the same, such as microscope slides, or alternatively receiving members 76 may include different types of items such as microscope slides and sample containers.

Cartridge mounting assembly 71 may be rotated so that selected fluid dispensing cartridges 10 may be positioned adjacent actuators 78, 79, 80 of actuator assembly 75. Alternatively, an actuator, such as the type shown as actuators 78, 79, and 80, may be positioned adjacent each cartridge 10 so that rotation of cartridge mounting assembly 71 is not required for actuation of a particular cartridge 10. Actuator assembly 75 can be any actuator device that triggers cartridge 10 to emit a controlled amount of fluid. For example, actuator assembly 75 may include a plurality of linear actuators, such as solenoids, that are aligned with exterior end 35 of pump piston 25 so that movement of the actuator applies force to move pump piston 25 within pump assembly 20.

Preferably, cartridge mounting assembly 71 may be both translated and rotated with respect to sample support assembly 72 so that an individual cartridge 10 can be selectively positioned above any receiving member 76. Once cartridge 10 is positioned above a selected receiving member 76, actuator assembly 75 triggers cartridge 10 to eject a controlled amount of fluid onto receiving member 76.

As seen in FIGS. 13 and 14, cartridge mounting assembly 71 may be rotatably coupled to a support member 81 and actuator assembly 75 may be fixedly attached to support member 81 so that cartridges 10 can be rotated with respect to actuator assembly 75. Preferably, support member 81 may be translated horizontally so the cartridges 10 can be both rotated and translated with respect to stationary receiving members 76. In this manner, a chosen cartridge 10 can be selectively positioned above any receiving member 76.

As seen in the illustrated embodiment, actuator assembly 75 may optionally include three actuators 78, 79, 80 used to dispense fluid onto respective rows 82, 83, 84 of receiving members 76. In operation, actuator 78 is adapted to dispense fluids onto receiving members 76 in row 82, actuator 79 is adapted to dispense fluids onto receiving members 76 in row 83 and actuator 80 is adapted to dispense fluids onto receiving members 76 in row 84. Of course, as will be understood by those of skill in the art, any number of actuators and/or receiving members can be employed without departing from the scope of the present invention.

As shown in FIG. 14, the system 70 optionally includes supply containers 85, waste containers 86 and valves 87. Supply containers 85 may be used to hold liquids such as water for rinsing receiving members 76 or reagents that may be distributed through a fluid distribution assembly included in system 70. Valves 87 can include switches for directing the flow of liquids through system 70 such as for rinsing receiving members 76. In addition, valves 87 may be used to direct the flow of liquids into waste containers 86 after the liquids have been used to rinse receiving members 76.

It is preferred that the shape of cartridges 10 is selected so that cartridge may only be installed in cartridge mounting assembly 71 in one orientation. For example, the cross-sectional shape of cartridge 10 taken through alignment surface 61 may be substantially trapezoidal and mounting apertures 74 in cartridge mounting assembly 71 are similarly shaped, thereby limiting the installation of cartridges 10 to one orientation. Additionally, one or more keys 66 may be included that are received within complementary features of mounting apertures 74. FIGS. 13 and 14 show examples of cartridges 10 having substantially trapezoidal cross-sections which are adapted to fit within substantially trapezoidal mounting apertures 74 (as shown in FIG. 13). In other embodiments, mounting apertures 74 and cartridges 10 have other similarly oriented shapes or include orientation features, such as a tab and slot, that limit installation of cartridge 10 in one orientation.

Figure 15:
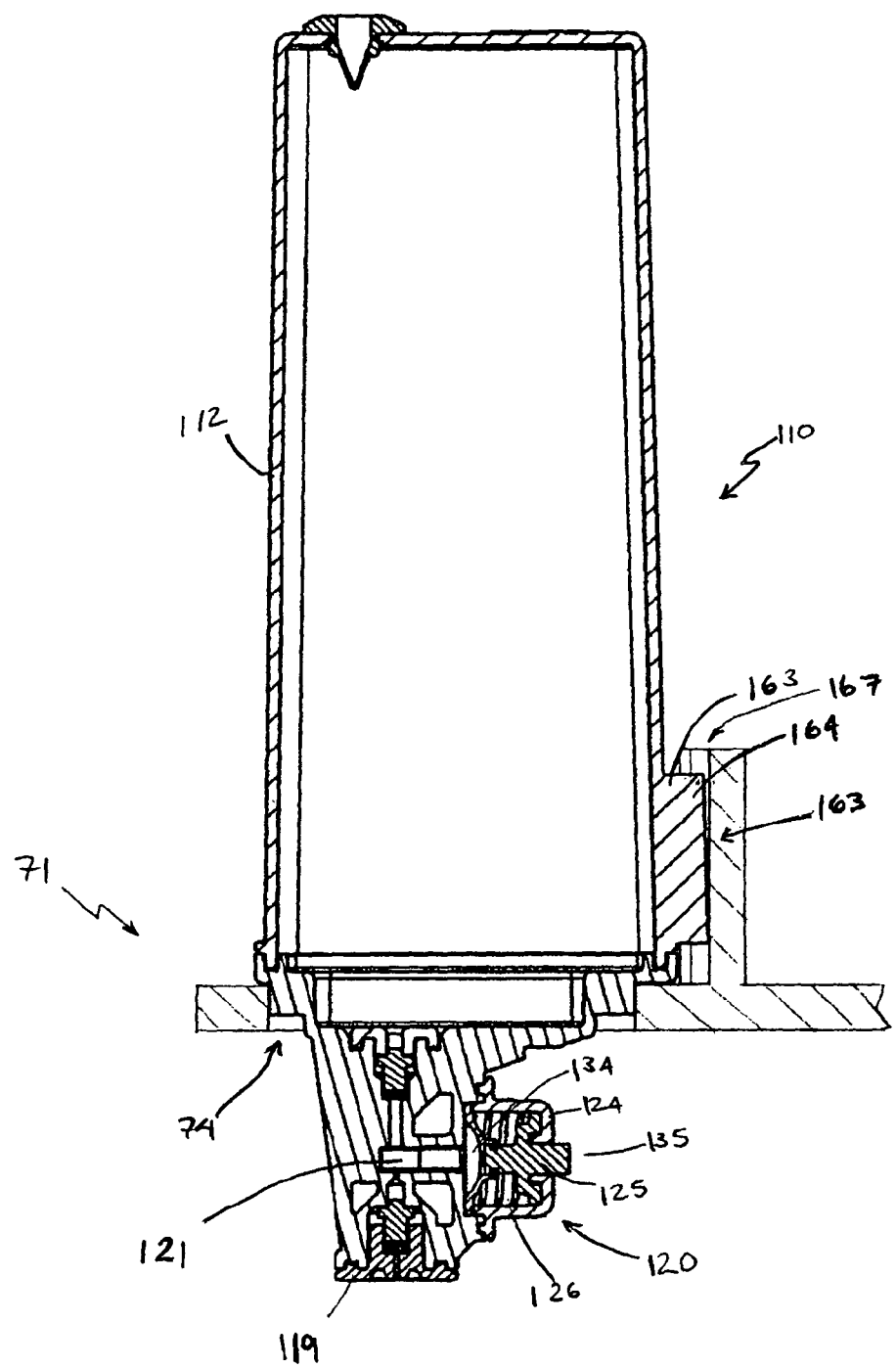
FIG. 15 is a cross-sectional view of a portion of a fluid dispensing system in which a fluid dispensing apparatus according to the present invention is mounted.
Figure 16:
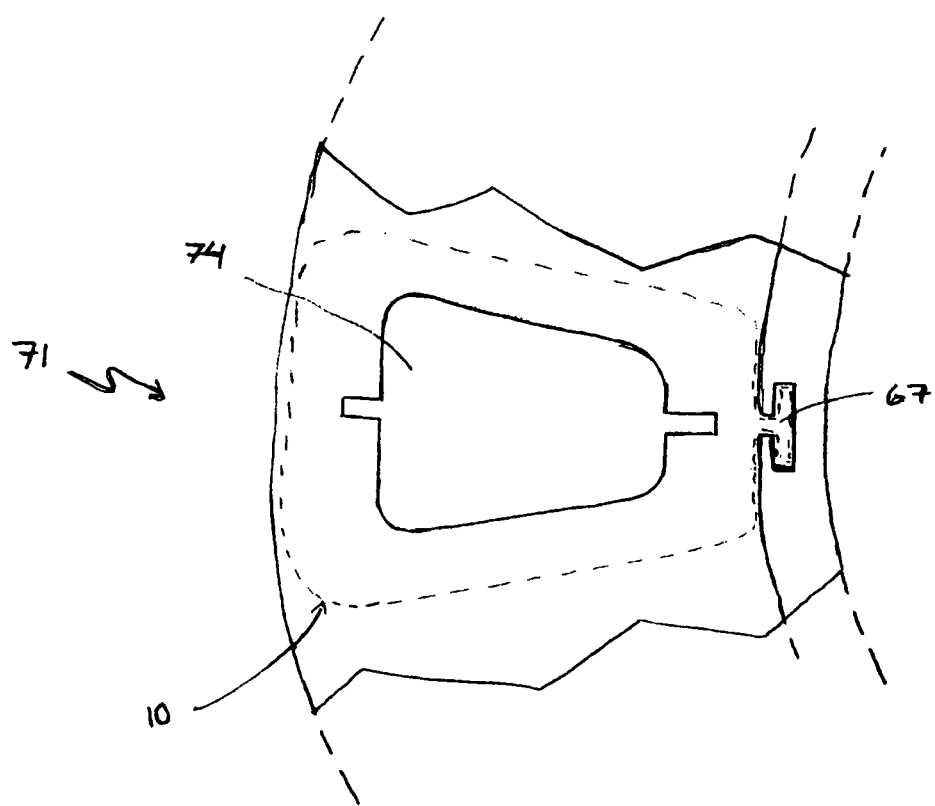
FIG. 16 is a top view of a portion of a fluid dispensing system.

Referring to FIGS. 15 and 16, an optional mounting feature included on cartridge 110 will be described. The mounting feature that can be utilized to releasably attach a cartridge 110 within a corresponding mounting aperture 74 of cartridge mounting assembly 71. As shown, cartridge 110 includes a mounting tab 163 that may be used to lock cartridge 110 into place after it has been aligned within a larger system. As shown, mounting tab 163 includes an outer portion 164 and an inner portion 165 that combine so that mounting tab 163 has a generally T-shaped cross section. The dimensions of outer portion 164 and/or inner portion 165 may vary over their length so that a friction fit between mounting tab 163 and a mounting slot 67 included in cartridge mounting assembly 71 may become tighter as mounting tab 163 is inserted further into slot 67.

Figure 17:
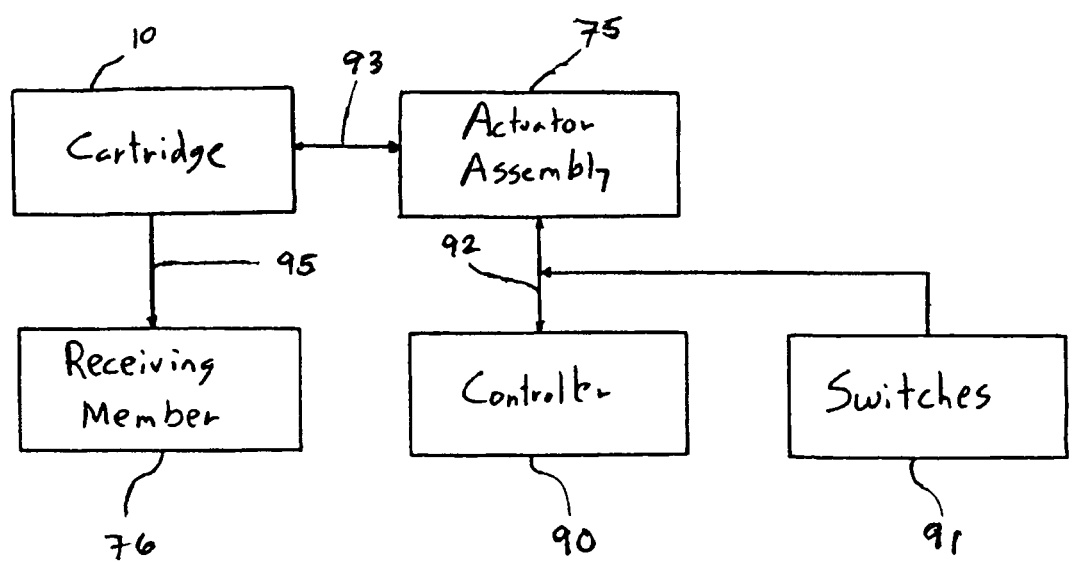
FIG. 17 is a flowchart of an embodiment of a fluid dispensing system incorporating a fluid dispensing apparatus in accordance with the present invention.

With reference to FIG. 17, actuator assembly 75 is preferably activated using a controller 90 and control switches 91 that may be used to activate any one of actuators 78, 79, 80. Preferably, controller 90 is a programmable computer. Controller also may be integrated into a main controller or control system for a fluid dispensing system 70 and programming steps for actuation of actuators 78, 79, 80 may be included in a main tissue processing program. Controller 90 may be any device that causes actuator assembly 75 to be automatically or manually activated. Furthermore, controller 90 may be located so that it does not move relative to cartridge mounting assembly 71. Alternatively, controller 90 may be located such that it moves relative to cartridge mounting assembly 71 and a hardwired or wireless communication link 92 may be provided between controller 90 and actuator assembly 75. Once activated, actuator assembly 75 applies a mechanical force 93 to pump assembly 20 of cartridge 10 to cause dispensing assembly 14 to dispense a stream or drip of fluid 94 onto receiving member 76.

Thus, it is seen that a fluid dispensing reagent cartridge is provided. One skilled in the art will appreciate that the present invention can be practiced by other than the preferred embodiments which are presented in this description for purposes of illustration and not of limitation, and the present invention is limited only by the claims that follow. It is noted that equivalents for the particular embodiments discussed in this description may practice the invention as well.

What is claimed is:

1. A fluid dispensing cartridge comprising:
a fluid reservoir;
a dispensing assembly fluidly coupled to the fluid reservoir including:
a dispensing housing having a cavity therein;
a pump assembly having a movable pump piston, a piston spring disposed around the pump piston and a deformable member positioned within a pump assembly housing, the deformable member positioned between the dispensing housing and the pump assembly housing and fluidly sealing an opening of the cavity, the opening laterally offset from an outlet of the dispensing assembly that is configured to allow fluid to flow out of the dispensing assembly, and the pump piston having a portion extending out of the pump housing and dimensioned to receive a force applied by an external actuator; and
a nozzle valve assembly comprising a deformable valve, a nozzle and a spring biasing the deformable valve in a direction of the nozzle, the deformable valve dimensioned to be deformed between a first position forming a fluid seal between a surface of the deformable valve and a fluid conduit formed within the nozzle and a second position removing the fluid seal to allow fluid to flow through the fluid conduit, and
wherein the cavity and the deformable member collectively define a metering chamber and the deformable member is configured to be deformed from a concave configuration in a rest position, the rest position corresponding to a first metering chamber volume, to a substantially flat configuration in an eject position, the eject position corresponding to a second metering chamber volume that is smaller than the first metering chamber volume; and
a mounting portion positioned between the fluid reservoir and the dispensing assembly, the mounting portion comprising an inner surface and an outer alignment surface extending from the fluid reservoir to the dispensing assembly, the inner surface defining a fluid chamber between the fluid reservoir and the dispensing assembly such that the mounting portion is in fluid communication with the fluid reservoir and the dispensing assembly, the entire outer alignment surface comprising a horizontal cross-sectional shape configured to be received in a similarly shaped receiving assembly and a mounting tab extending from the outer alignment surface, the mounting tab configured to be received within a mounting slot of the receiving assembly.

2. The fluid dispensing cartridge of claim 1 further comprising a reservoir valve located between the fluid reservoir and the metering chamber that is configured to allow fluid to flow from the reservoir to the metering chamber.

3. The fluid dispensing cartridge of claim 2 wherein the deformable valve is located between the metering chamber and the nozzle.

4. The fluid dispensing cartridge of claim 3 wherein the deformable valve comprises a raised member extending from a surface of the deformable valve and the raised member forms the fluid seal against a wall of the fluid conduit.

5. The fluid dispensing cartridge of claim 2 wherein the reservoir valve is a one-way valve configured to allow fluid to flow from the reservoir into the dispensing assembly and the nozzle valve assembly is a one-way valve configured to allow fluid to flow from the dispensing assembly out of the cartridge.

6. The fluid dispensing cartridge of claim 2 further comprising a filter interposed between the reservoir valve and the fluid reservoir.

7. The fluid dispensing cartridge of claim 6 wherein the filter is a cap that retains the reservoir valve in the dispensing housing.

8. The fluid dispensing cartridge of claim 1 the fluid conduit of the nozzle defines an outlet of the dispensing assembly.

9. The fluid dispensing cartridge of claim 8 wherein the nozzle is constructed from a hydrophobic material.

10. The fluid dispensing cartridge of claim 1 further comprising a one-way valve coupled to the fluid reservoir that is configured to allow fluid to flow into the reservoir from the environment.

11. The fluid dispensing cartridge of claim 1 wherein the deformable member is biased to the rest position.

12. The fluid dispensing cartridge of claim 11 wherein the piston is configured such that translation of the piston deforms the deformable member between the rest position and the eject position.

13. The fluid dispensing cartridge of claim 1 wherein the horizontal cross-sectional shape of the mounting portion is configured to be received in the similarly shaped receiving assembly in one predetermined orientation.

14. The fluid dispensing cartridge of claim 1 wherein the horizontal cross-sectional shape is substantially trapezoidal.

* * * * *

UNITED STATES PATENT AND TRADEMARK OFFICE
CERTIFICATE OF CORRECTION

PATENT NO. : 8,459,509 B2
APPLICATION NO. : 11/441668
DATED : June 11, 2013
INVENTOR(S) : Xuan S. Bui It is certified that error appears in the above-identified patent and that said Letters Patent is hereby corrected as shown below:

In the Claims, Column 15, Claim 8, line 19, please insert --wherein-- after "claim 1".

Signed and Sealed this
Tenth Day of September, 2013

Teresa Stanek Rea
*Acting Director of the United States Patent and Trademark Office*